(12) United States Patent
Chappell et al.

(10) Patent No.: US 6,605,764 B1
(45) Date of Patent: *Aug. 12, 2003

(54) PATHOGEN- OR ELICITOR-INDUCIBLE TRANSCRIPTION REGULATORY ELEMENT FROM THE TOBACCO 5-EPI-ARISTOLOCHENE SYNTHASE GENE AND PLANTS TRANSFORMED THEREWITH

(75) Inventors: Joseph Chappell, Lexington, KY (US); Shaohui Yin, Ardmore, OK (US); Catherine Cornett, Florence, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/435,380

(22) Filed: Nov. 5, 1999

Related U.S. Application Data

(63) Continuation of application No. 08/443,639, filed on May 18, 1995, now Pat. No. 5,981,843.

(51) Int. Cl.⁷ .............................. A01H 5/00; C12N 5/14

(52) U.S. Cl. .................... 800/317.3; 435/419; 800/298; 800/317

(58) Field of Search .............................. 435/320.1, 419, 435/468; 536/24.1; 800/278, 279, 298, 301, 317, 317.3

(56) References Cited

U.S. PATENT DOCUMENTS

| | | | | |
|---|---|---|---|---|
| 5,550,228 | A | 8/1996 | Godiard et al. | 536/24.1 |
| 5,723,760 | A | 3/1998 | Strittmatter et al. | 800/205 |
| 5,866,776 | A | 2/1999 | de Wit | 800/205 |
| 5,981,843 | A | 11/1999 | Chappell et al. | 800/301 |

FOREIGN PATENT DOCUMENTS

| | | |
|---|---|---|
| EP | 0 332 104 | 9/1989 |
| EP | 0 392 225 | 10/1990 |
| WO | WO 90/05187 | 5/1990 |
| WO | WO 91/15585 | 10/1991 |
| WO | WO 93/06710 | 4/1993 |
| WO | WO 93/19188 | 9/1993 |

OTHER PUBLICATIONS

Kim Y, et al. "A 20 nucleotide upstream element is essential for the nopaline synthase (nos) promoter activity." Plant Mol. Biol. 24: 105–177, 1994.*
Benfey PN, et al. "The cauliflower mosaic virus 35S promoter: Combinatorial regulation of transcription in plants." Science 250: 959–966, Nov. 1990.*
Oommen, A, et al. "The elicitor–inducible alfalfa isoflavone reductase promoter confers differential patterns of developmental expression in homologous and heterologous transgenic plants." Plant Cell 6: 1789–1803, Dec. 1994.*
Mohan R, et al. "Developmental and tissue–specific expression of a tomato anionic peroxidase (tap1) gene by a minimal promoter, with wound and pathogen induction by an additional 5'–flanking region." Plant Mol. Biol. 22: 475–490, 1993.*
Kay R, et al. "Duplication of CaMV 35S promoter sequences creates a strong enhancer for plant genes." Science 236: 1299–1302, Jun. 1987.*
Albersheim and Valent, "Host–Pathogen Interactions in Plants," *J. Cell Biology* 78:627–643 (1978).
Back et al., "Expression of a Plant Sesquiterpene Cyclase Gene in *Escherichia coli*," *Archives of Biochemistry and Biophysics* 315:527–532 (1994).
Blein et al., "Responses of Cultured Tobacco Cells to Cryptogein, a Proteinaceouse Elicitor from *Phytophthora cryptogea*," *Plant Physiol.* 95:486–491 (1991).
Bonnet et al., "Diversity in Pathogenicity to Tobacco and in Elicitin Production Among Isolates of *Phytophthora parasitica*," *J. Phytopathology* 141:25–37 (1994).
Chappell et al., "Elicitor–Inducible 3–Hydroxy–3–Methoylglutaryl Coenzyme A Reductase Activity Is Required For Sesquiterpene Accumulation in Tobacco Cell Suspension Cultures," *Plant Physiol.* 97:693–698 (1991).
Colby et al., "4S–Limonene Synthase from the Oil Glands of Spearmint (*Mentha spicata*)," *J. Biol. Chem* 268:23016–23024 (1993).
Culver et al., "Tobacco Mosaic Virus Elicitor Coat Protein Genes Produce a Hypersensitive Phenotype in Transgenic *Nicotiana Sylvestris* Plants," MPMI 4:458–463 (1991).
Facchinni and Chappell, "Gene Family for an Elicitor–Induced Sesquiterpene Cyclase in Tobacco," *Proc. Natl. Acad. Sci. USA* 89:11088–11092 (1992).
Gough et al., "Developmental and Pathogen–Induced Activation of an msr Gene, str 246C, from Tobacco Involves Multiple Regulatory Elements," *Mol. Gen. Genet.* 247:323–337 (1995).
Guedes et al., Accumulation of six Sesquiterpenoid Phytoalexins in Tobacco Leaves Infiltrated with *Pseudomonas Lachrymans* Phytochemistry 21:2987–2988 (1982).
Hammond–Kosak et al., "Developmentally Regulated Cell Death on Expression of the Fungal Avirulence Gene Avr9 in Tomato Seedlings Carrying the Disease–Resistance Gene Cf–9," *Proc. Natl. Acad. Sci* 91:10455–10449 (1994).
Hohn et al., "Expression of a Fungal Sesquiterpene Cyclase Gene in Transgenic Tobacco," *Plant Physiol.* 97:460–462 (1991).

(List continued on next page.)

Primary Examiner—Amy J. Nelson
(74) Attorney, Agent, or Firm—Clark & Elbing LLP

(57) ABSTRACT

A tobacco epi-5-aristolochene synthase transcriptional regulatory element functional in plants, plant tissue and in plant cells for pathogen inducible gene expression and a method for increasing the transcriptional expression of downstream genetic information in plants, plant tissue and plant cells are disclosed.

11 Claims, 4 Drawing Sheets

OTHER PUBLICATIONS

Figure 1:
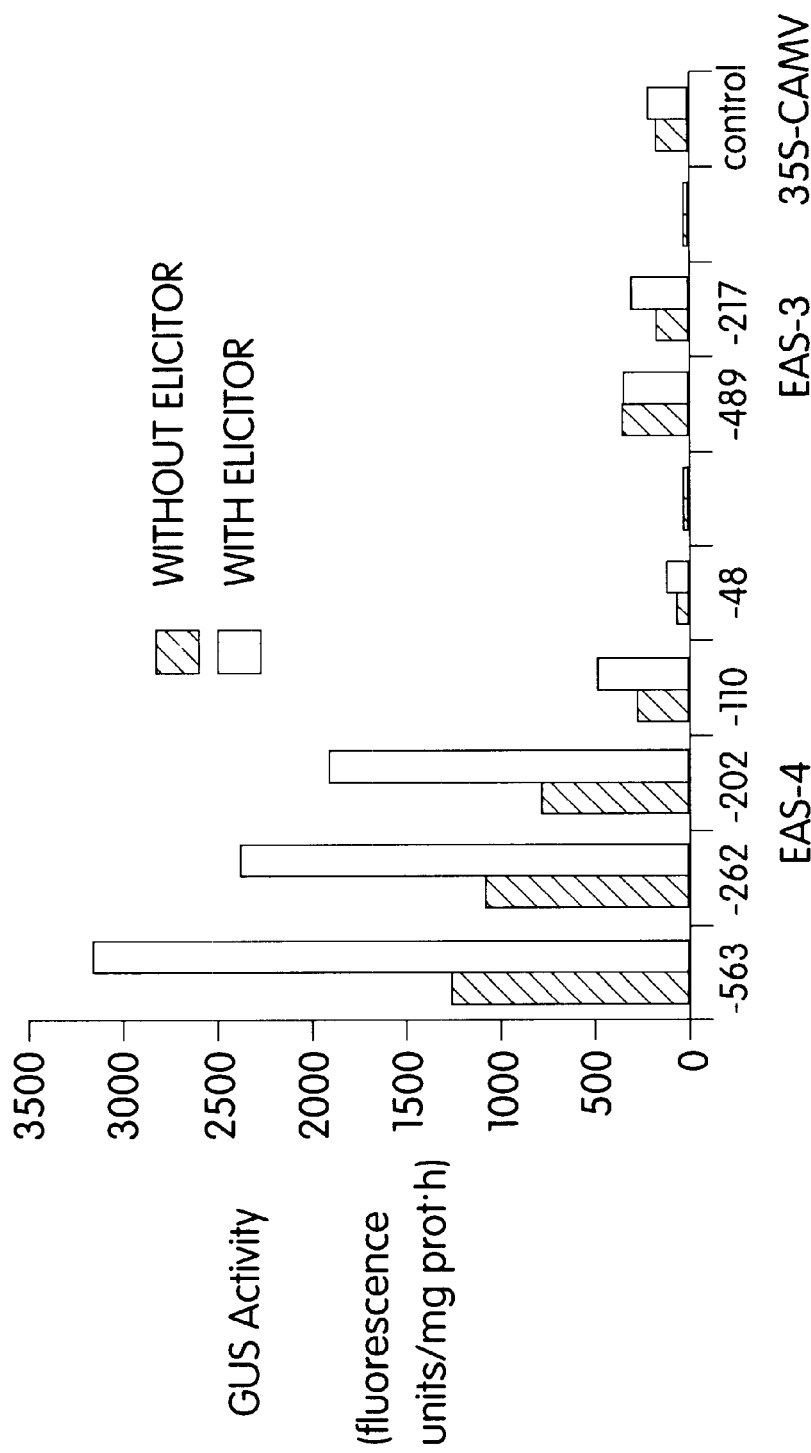

Huang et al., "Bacterial Induced Activation of an *Arabidopsis* Phenylalanine Ammonia–Lyase Promoter in Transgenic Tobacco Plants," *Plant Science* 98:25–35 (1994).

Huet and Pernollet, "Amino Acid Sequence of Cinnamomin, a New Member of the Elicitin Family, and its Comparison to Cryptogein and Capsicein," *FEB* 257:302–306 (1989).

Huet et al., "Structures of Elicitn Isoforms Secreted by *Phytophthora Drechsleri,*" *Phytochemistry* 31:1471–1476 (1992).

Kamoun et al., "Incompatible Interactions Between Crucifers and *Xanthomonas campestris* Involve a Vascular Hypersensitive Response: Role of the hrpX Locus," *Molecular Plant–Microbe Interactions* 5:22–33 (1992).

Kamoun et al., "A Gene Encoding a Host–Specific Elicitor Protein of *Phytophthora Parasitica,*" *Molecular Plant–Microbe Interactions* 6:573–581 (1993).

Koziel MG, et al., "Optimizing Expression of Transgenes with an Emphasis on Post–Transcriptional Events," *Plant Mol. Biol.* 32:393–405 (1996).

Meier et al., "Elicitor–Inducible and Constitutive in Vivo DNA Footprints Indicate Novel cis–Acting Elements in the Promoter of a Parsley Gene Encoding Pathogenesis–Related Protein 1," *The Plant Cell* 3:309–315 (1991).

Milat et al., "Capsidiol and Ethylene Production by Tobacco Cells in Response to Cryptogein, An Elicitor From *Phytophthora Cryptogea,*" *Phytochemistry* 30:2171–2173 (1991).

Nespoulous et al., "Structure–Function Relationships of α and β Elicitins, Signal Proteins Involved in the Plant–Phytophthora Interaction," *Planta* 186:551–557 (1992).

Newman et al., "Protein Binding Sites in the Promoter of a Tobacco Phytoalexin Biosynthetic Gene," *Supplement to Plant Physiology* 108:575 (1995).

Ricci et al., "Structure and Activity of Proteins from Pathogenic Fungi *Phytophthora* Eliciting Necrosis and Acquired Resistance in Tobacco," *Eur. J. Biochem.* 183:555–563 (1989).

Saiki et al., "Primer–Directed Enzymatic Amplification of DNA with a Thermostable DNA Polymerase," *Science* 239:487–491 (1988).

Samac et al., "Developmental and Pathogen–Induced Activation of the Arabidopsis Acidic Chitinase Promoter," *The Plant Cell* 3:1063–1072 (1991).

Sequeira, "Mechanisms of induced Resistance in Plants," *Ann. Rev. Microbiol.* 37:51–79 (1983).

Smith et al., "Antisense RNA Inhibition of Polygalacturonase Gene Expression in Transgenic Tomatoes," *Nature* 334:724–726 (1988).

Stam et al., "The Silence of Genes in Transgenic Plants," *Ann. Bot.* 79:3–12 (1997).

Tedford et al., "A Detached–Leaf Technique for Detecting Resistance to *Phytophthora parasitica* var. Nicotianae in Tobacco," *Plant Disease* 74:313–316 (1990).

Van de Rhee et al., "Analysis of Regulatory Elements Involved in the Induction of Two Tobacco Genes by Salicylate Treatment and virus Infection," *The Plant Cell* 2:357–366 (1990).

Vogell and Chappell, "Regulation of a Sesquiterpene Cyclase in Cellulase–Treated Tobacco Cell Suspension Cultures," *Plant Physiol.* 94:1860–1866 (1990).

Vogeli et al., "Purification and Characterization of an Inducible Sesquiterpene Cyclase from Elicitor–Treated Tobacco Cell Suspension Cultures," *Plant Physiol.* 93:182–187 (1990).

Wehner et al., "Molecular Structures and Genetic Regulation of SFA, a Gene Responsible for Resistance to Formaldehyde in *Saccharomyces cerevisiae*, and Characterization of its Protein Product," *Mol. Gen. Genet* 237:351–358 (1993).

Yin et al., "Elicitor–Induced Activation of a Tobacco Sesquiterpene Cyclase Promoter," *Supplement to Plant Physiology* 108:574 (1995).

Yu, "Elicitins from *Phytophthora* and Basic Resistance in Tobacco," *Proc. Natl. Acad. Sci. USA* 92:4088–4094 (1995).

Zhu et al., "Accurate in vitro Transcription From Circularized Plasmid Templates by Plant Whole Cell Extract," *The Plant Journal* 7:1021–1030 (1995).

* cited by examiner

PATHOGEN- OR ELICITOR-INDUCIBLE TRANSCRIPTION REGULATORY ELEMENT FROM THE TOBACCO 5-EPI-ARISTOLOCHENE SYNTHASE GENE AND PLANTS TRANSFORMED THEREWITH

This application is a continuation of Ser. No. 08/443,639, now U.S. Pat. No. 5,981,843, which was filed on May 18, 1995, the disclosure of which is hereby incorporated by reference.

This invention was made, at least in part, with funding from the National Science Foundation and the United States Department of Agriculture. Accordingly, the United States Government may have certain rights in this invention.

THE FIELD OF THE INVENTION

The field of this invention is the area of plant molecular biology, and it relates in particular to transcription regulatory elements: a qualitative regulatory sequence which positively regulates downstream gene expression in plant tissue in response to the stress of an invading microbial pathogen, an elicitor, or other inducing chemical signals and quantitative regulatory sequences which increase the transcriptional expression of associated sequences.

THE BACKGROUND OF THE INVENTION

In plants, disease resistance to fungal, bacterial and viral pathogens is associated with a plant response termed the hypersensitivity response (HR). In the HR, the site in the plant where the potential phytopathogen invades undergoes localized cell death, and it is postulated that this localized plant cell death aspect of the HR contains the invading microorganism or virus, thereby protecting the remainder of the plant. Other plant defenses include the production of phytoalexins (antibiotics) and/or lytic enzymes capable of averting pathogen ingress and/or cell wall modifications which strengthen the plant cell wall against physical and/or enzymatic attack.

The HR of plants, including tobacco, can include phytoalexin production as part of the response to invading microorganisms. One class of compounds made by tobacco (*Nicotiana tabacum*) in response to microbial invaders are the sesquiterpenes.

Cell suspension cultures have provided useful information regarding the regulation of terpene synthesis. Isoprenoids are ubiquitous in nature, and the early portions of the biosynthetic pathway are shared with the biosynthetic pathway for other isoprenoid compounds such as sterols, carotenoids, dolichol and ubiquinone and growth regulators (e.g., gibberellic acid), which are classified as primary metabolites. Isoprenoid compounds classified as secondary metabolites are not essential for growth, and include mono-, sesqui- and diterpenoids. These secondary metabolite isoprenoids are important mediators of interactions between the plant and its environment.

A variety of compositions can serve as elicitors of plant phytoalexin synthesis. These include, but are not limited to, one or more toxic ions, e.g., mercuric ions, other chemically defined compositions, metabolic inhibitors, cell wall glycans, certain glycoproteins, certain enzymes, fungal spores, chitosans, certain fatty acids and certain oligosaccharides derived from plant cell walls [See, e.g., Sequeira, L. (1983) *Annu. Rev. Microbiol.* 37:51–79 and references cited therein]. Epi-5-aristolochene synthase (EAS) activity in tobacco plants has been shown to be induced by cell wall fragments of certain Phytophthora species and by *Tricho-*

*derma reesei* cellulase but not *Aspergillus japonicum* pectolyase [Chappell et al. (1991) *Plant Physiol.* 97:693–698]. Attack by other plant pathogens or an avirulent related strain can also induce phytoalexin synthesis; for example, *Pseudomonas lachrymans* induces sesquiterpenoid synthesis in tobacco [Guedes et al. (1982) *Phytochemistry* 21:2987–2988].

Elicitins are proteins which are produced by plant pathogens and potential plant pathogens, which proteins induce the HR in tobacco plants. Amino acid and nucleotide coding sequences for an elicitin of *Phytophthora parasitica* have been published [Kamoun et al. (1993) *Mol. Plant-Microbe Interactions* 6:573–581]. Plant pathogenic viruses including, but not limited to, Tobacco Mosaic Virus (TMV) induce the HR in infected plants. Bacteria which infect plants also can induce HR and thereby disease resistance; representative bacteria eliciting HR include, but are not limited to, Agrobacterium species, Xanthomonas species and *Pseudomonas syringae*. Plant pathogenic fungi (and certain avirulent strains as well) also induce the HR response, where these include, but are not limited to, *Phytophthora parasitica* and *Peronospora tabaci*.

When tobacco cell suspension cultures are treated with an elicitor, squalene synthetase is suppressed, thus stopping the flow of common biosynthetic precursors into sterols. The concomitant induction of sesquiterpene cyclase gene expression causes the flow of precursors in sesquiterpenes. The first step in the pathway from farnesyl diphosphate to the sesquiterpene phytoalexin capsidiol in elicitor-induced tobacco tissue is catalyzed by 5-epi-aristolochene synthase (EAS), a sesquiterpene cyclase. The coding sequence and deduced amino acid sequence for one member of the EAS gene family of tobacco have been published [Facchini and Chappell (1992) *Proc. Natl. Acad. Sci. USA* 89:11088–11092]. The transcriptional expression of one or more members of the EAS gene family is induced in response to elicitors.

There is a long felt need in the art for methods of protecting plants, particularly crop plants, from infection by plant pathogens, including but not limited to, phytopathogenic viruses, fungi and/or bacteria. Especially important from the standpoint of economics and environmental concerns are biological or "natural" methods rather than those which depend on the application of chemicals to crop plants. There is also a long felt need in the art for plant transcriptional regulatory sequences for use in controlling the expression of heterologous DNA sequences in transgenic plants.

SUMMARY OF THE INVENTION

The present invention provides qualitative transcriptional regulatory sequences which regulate downstream gene expression in plant tissue in response to one or more elicitors, other defined inducing compounds or in response to the stress of an invading phytopathogen (the inducible transcription regulatory sequence) and quantitative transcription regulatory sequences which increase the transcription of downstream sequences (the transcription-enhancing sequence). As specifically exemplified herein, these transcriptional regulatory sequences are found in nature upstream and operatively linked to the epi-5-aristolochene synthase gene (EAS4) of tobacco; when operatively linked to a coding sequence (and in the presence of an operatively linked promoter element, from the EAS4 gene or from a heterologous plant-expressible gene) these sequences mediate the inducible transcriptional expression of that coding sequence when the plant or plant tissue is invaded by a potential phytopathogen (virus, fungus or bacterium) or in response to elicitors such as *Trichoderma viride* cellulase or plant or fungal cell wall fragments for plants, plant tissue and/or plant suspension culture cells. That potential plant pathogen can be a virus including, but not limited to, tobacco mosaic virus or tobacco vein mottle virus, a bacterium including, but not limited to, *Pseudomonas syringae, Xanthomonas campestris* or *Agrobacterium tumefaciens,* or a fungus including, but not limited to, a species of Phytophthora (e.g., *P. parasitica*) or Peronospora (e.g., *P. tabaci*). The EAS4 promoter comprising the inducible transcription regulatory element(s) and the transcription-enhancing sequence(s) are disclosed herein as SEQ ID NO:2. In SEQ ID NO:2, the CAAT-homologous sequence of the EAS4 promoter is located at nucleotides 513 to 516, and the TATA-sequence motif is located at nucleotides 540 to 543.

The minimal inducible transcriptional regulatory element within the *N. tabacum* EAS4 upstream sequence is from nucleotide 458 to nucleotide 473 of SEQ ID NO:2; optionally from 454 to 473; more preferably from nucleotide 413 to 473 in SEQ ID NO:2 provides the inducible transcriptional regulatory element sequences.

Another aspect of the present invention is the transcription-enhancing element derived from the EAS4 promoter and promoter-associated sequences. When operatively linked upstream of a promoter, particularly upstream of a minimal promoter, this element increases the transcriptional expression of the downstream sequences. Transcriptional enhancing activity is mediated by DNA sequence information in the region between nucleotides 371 and 463 in SEQ ID NO:2. Preferably, an EAS4-derived transcription-enhancing sequence comprises a nucleotide sequence as given in SEQ ID NO:2 from nucleotide 371 to nucleotide 463, more preferably from nucleotide 1 to nucleotide 463, and optionally from nucleotide 1 to about nucleotide 1040 of SEQ ID NO:7.

Also provided by the present invention is an expression cassette into which a coding sequence of interest can be cloned, and said coding sequence of interest can be expressed in plant tissue after the introduction of the unit into plant tissue. A preferred coding sequence of interest is that for the ParA1 elicitin protein of *Phytophthora parasitica*. The coding sequence and deduced amino acid sequence for the ParA1 protein, including the signal peptide, are given in SEQ ID NOs:16 and 17, respectively. The coding sequence and deduced amino acid sequences of the nature ParA1 protein as amplified and described hereinbelow are given in SEQ ID NOs:18 and 19, respectively. Transcription is regulated by the EAS4 promoter sequence and promoter-associated regulatory element or by at least one of the transcription regulatory elements (inducible and/or transcription-enhancing) operably linked to transcription initiation sequences and a heterologous DNA sequence to be expressed.

A further aspect of the present invention are transgenic plant cells, plant tissue and plants which have been genetically engineered to contain and express a nucleotide sequence of interest, preferably a coding sequence, an antisense sequence or other sequence, under the regulatory control of the inducible transcription regulatory element. It is an object of this invention to provide the nucleotide sequences which mediate the induction of the expression of a downstream coding sequence in response to elicitor exposure, potential phytopathogen invasion in a plant, or certain other exogenous inducing signals such as exposure to methyl jasmonate and ethylene. An exemplary elicitor inducible transcription regulatory element is that from the 5' flanking region of the EAS4 gene of *Nicotiana tabacum;* as specifically exemplified herein, this sequence is presented in SEQ ID NO:2 from nucleotide 410 to nucleotide 472. Equivalents of the exemplified nucleotide sequence are those nucleotide sequences which similarly direct the induction of the expression of downstream nucleotide sequences. Preferably the inducible transcription regulatory element is associated with EAS4 promoter and promoter-associated sequences (e.g., the combination having the nucleotide sequence as given in SEQ ID NO:2 from nucleotide 410 to nucleotide 573 of SEQ ID NO:2, preferably from nucleotide 361 to 573 of SEQ ID NO:2, more preferably the sequence from 1 to 573 of SEQ ID NO:2).

BRIEF DESCRIPTION OF THE DRAWINGS

FIG. 1 presents data for transient expression experiments for GUS regulated by the EAS3 and EAS4 promoter region sequences in comparison to a CaMV 35S-GUS construct (Cauliflower Mosaic Virus 35S promoter—β-glucuronidase reporter gene). These experiments were carried out in tobacco protoplasts into which the DNA constructs had been electroporated. "Uninduced" levels of expression for the EAS-GUS constructs were relatively high because fungal enzymes which digest plant cell walls were used in the preparation of the protoplasts. The y-axis shows units of GUS activity and the 5' extents of the EAS upstream sequences are given below each bar on the graph. As above, the numbering is relative to the natural transcription start site of EAS4 (or the corresponding base of EAS3); in EAS4 (SEQ ID NO:2) the start site is at nucleotide 573; in EAS3 (SEQ ID NO:1) the potential transcription start site is at nucleotide 489.

FIGS. 2A–2B present information concerning the reporter gene expression directed by the instant inducible transcription regulatory element. FIG. 2A presents a schematic of experiments carried out with the EAS4 promoter region controlling the expression of the GUS reporter gene in stably transformed transgenic plants. FIG. 2B presents the results of "gain of function" assays for the EAS4 promoter-associated sequence-regulating expression of the GUS reporter gene via the CaMV 35S minimal promoter. In both FIGS. 2A and 2B, numbering for the EAS4 upstream region reflect numbering relative to the natural transcription start site of the EAS4 gene (See also SEQ ID NO:2 wherein the transcription start site corresponds to nucleotide 573). In both FIGS. 2A and 2B, the GUS expression is measured in Fluorescence units per milligram protein.

FIG. 3 is a schematic of the genetic manipulation leading to generation of disease-resistant plants. The coding sequence for the ParA1 elicitin is isolated by PCR so as to have BamHI and SstI ends. $gEAS4_{600}$-GUS-pBI101, which directs the expression of the GUS reporter gene under the regulatory control of the EAS promoter, is digested with BamHI and SstI to release the GUS reporter gene. Then the BamHI/SstI-digested parA1 amplimer is ligated to the large fragment produced after digestion of $gEAS4_{600}$-GUS-pBI101 to produce $gEAS4_{600}$-parA1-pBI101, from which the ParA1 elicitin in plant cells or plant tissue is synthesized after induction with a suitable elicitor.

DETAILED DESCRIPTION OF THE INVENTION 5-epi-aristolochene synthase (EAS) is a key enzyme in the synthesis of sesquiterpenoid phytoalexins, for example, in solanaceous plants, including but not limited to Nicotiana species (e.g., *tabacum*), *Capsicum annum* and *Hyoscyamus*

*muticus*. EAS catalyzes the reaction of farnesyl diphosphate to (+) gemacrene A to eudesmane carbocation to 5epi-aristolochene. Other plants, such as the crucifers, also have sesquiterpene cyclase enzymes.

Treatments which induce host defensive responses in plant tissue or plant cells such as phytoalexin synthesis include cell wall fragments of Phytophthora species and *Trichoderma viride* cellulase. However, pectolyase from *Aspergillus japonicus* does not function as an elicitor in tobacco cell culture. Elicitors which induce sesquiterpenoid phytoalexin synthesis have been shown to function at the level of controlling transcription of key biosynthetic enzymes [Vogeli and Chappell (1990) *Plant Physiol.* 94:1860–1866]. Similar patterns have been observed in other plants, but no transcriptional control sequences which mediate gene induction in response to phytopathogen challenge have been described.

Tobacco (*N. tabacum*) contains an EAS gene family with some 12–15 members, the coding sequence of EAS4 has been published [Facchini and Chappell (1992) supra]. However, since that time, the present inventors have discovered that the EAS3 does not appear to be expressed in response to the elicitor treatment, and surprisingly, the nucleotide sequences upstream of EAS3 do not appear to mediate the induction of a reporter gene in a chimeric gene construct in elicitor-induced transgenic cell culture. It is noted that the translation start site was incorrectly identified in the 1992 Facchini and Chappell publication. The nucleotide sequence of a genomic clone of EAS4, as it appears in Facchini and Chappell (1992) supra is presented in SEQ ID NO:7, with the deduced amino acid sequence being given in SEQ ID NO:8.

Other aspects of a plant's defenses against invasion and infection by a phytopathogenic microorganism include the hypersensitive response, which is characterized by necrosis, i.e., programmed cell death in the localized area of attack by the plant pathogen. Elicitor treatments as described above can also induce the necrotic response.

Elicitins are proteins produced by fungal plant pathogens, which proteins elicit a hypersensitive response in an infected plant. Generally, but not necessarily, localized cell death is the result of the elicitin-induced response in the infected (or challenged) plant tissue. These responses mediate full or partial resistance to destructive infection by the invading, potentially plant pathogenic microorganism. For the purposes of the present invention, a protein of a plant pathogen or potential plant pathogen which induces the hypersensitive response in plant tissue after invasion of that plant tissue or after expression of that coding sequence in the plant tissue is considered to fall within a broad definition of an elicitin.

A relatively well-known elicitin of a plant-pathogenic fungus is the ParA1 protein of *Phytophthora parasitica*. The parA1 locus is a member of a gene family [Ricci et al. (1989) *Eur. J. Biochem.* 183:555–563]. The coding and amino acid sequences for the parA1 gene product are described in Kamoun et al. (1993) *Mol. Plant-Microbe Interact.* 4:423–432 and in SEQ ID NOs:12 and 13 herein.

Other phytopathogen proteins with potential elicitin activity have been characterized as to amino acid sequences and other properties [See, e.g., Nespoulous et al. (1992) *Plants* 186:551–557; Huet et al. (1992) *Phytochemistry* 31:1471–1476; Huet and Pernollet (1992) *FEBS Lett.* 257:302–306; Kamoun et al. (1993) *Mol. Plant-Microbe Interact.* 5:22–33]. Keen, N. T. (1990) *Annu. Rev. Phytopathol.* 24:447–463 has described an avirulence gene of *Fulva fulvia*. Hammond-Kosack et al. (1994) *Proc. Natl. Acad. Sci. USA* 91:10445–10449 have described the avr gene of *Cladosporium fulvum*, which functions in the same way as the *P. parasitica* elicitin.

Certain bacterial plant pathogens also express proteins with similar effects on the hypersensitivity response as those of the *P. parasitica* ParA1 elicitin. For the purposes of the present invention, these proteins fall within the scope of the term "elicitin." Multiple homologs of the avirulence gene avrBs3 of *Xanthomonas campestris pv. vesicatoria* have been detected in other *X. campestris* pathovars [Bonas et al. (1989) *Mol. Gen. Genet.* 218:127–136; Knoop et al. (1991) *J. Bacteriol.* 173:7142–7150] and in other species of Xanthomonas [De Feyter and Gabriel (1991) *Mol. Plant-Microbe Interact.* 4:423–432; Hopkins et al. (1992) *Mol. Plant-Microbe Interact.* 5:451–459]. The avrD gene of *Pseudomonas syringae pv. tomato* can confer avirulence; *P. syringae pv. glycinea* expresses an altered avrD gene product [Kobayashi et al. (1990) *Mol. Plant-Microbe Interact.* 3:103–111].

It is understood that to be useful in the present invention as it applies to creating transgenic plants with improved disease resistance traits using an elicitin coding sequence expressed under the regulatory control of a pathogen-response transcription regulatory element (and with a minimal promoter functional in those plants) that elicitin protein must be capable of promoting expression of defense genes (including but not limited to those genes governing phytoalexin synthesis, the hypersensitive response and/or localized necrosis) in those plants. Many functional combinations of plant and phytopathogen are known to the art, and the skilled artisan knows how to test the functioning of a particular elicitin in a particular plant tissue (or cells) in the turning on of programmed cell death or phytoalexin synthesis or the like. It is also understood that treatment of plant cells or tissue with compositions such as certain fungal cellulases or certain plant polysaccharide fragments can also induce the host defensive (i.e., hypersensitive) response. Such treatments are used as models for actual plant pathogen attack or invasion.

A non-naturally occurring recombinant nucleic acid molecule, e.g., a recombinant DNA molecule, is one which does not occur in nature; i.e., it is produced either by natural processes using methods known to the art, but is directed by man to produce a desired result or it has been artificially produced from parts derived from heterologous sources, which parts may be naturally occurring or chemically synthesized molecules or portions thereof, and wherein those parts have been joined by ligation or other means known to the art.

A transgenic plant is one which has been genetically modified to contain and express heterologous DNA sequences, either as regulatory RNA molecules or as proteins. As specifically exemplified herein, a transgenic plant is genetically modified to contain and express a heterologous DNA sequence operably linked to and under the regulatory control of transcriptional control sequences by which it is not normally regulated, i.e., under the regulatory control of the inducible transcriptional control sequences of the EAS4 gene of *Nicotiana tabacum.* As used herein, a transgenic plant also refers to those progeny of the initial transgenic plant which carry and are capable of expressing the heterologous coding sequence under the regulatory control of the qualitative and/or quantitative transcription control sequences described herein. Seeds containing transgenic embryos are encompassed within this definition.

When production of a heterologous gene or coding sequence of interest is desired under conditions of potential pathogen invasion or inducer (e.g., elicitor) treatment, that coding sequence is operably linked in the sense orientation to a suitable promoter and under the regulatory control of the inducible regulatory sequences, in the same orientation as the promoter, so that a sense (i.e., functional for translational expression) mRNA is produced. A transcription termination signal functional in a plant cell can be placed downstream of the coding sequence, and a selectable marker which can be expressed in a plant, can be covalently linked to the inducible expression unit so that after this DNA molecule is introduced into a plant cell or tissue, its presence can be selected and plant cells or tissue not so transformed will be killed or prevented from growing. Similarly, a heterologous coding sequence can be expressed under the regulatory control of the inducible transcription regulatory element or the transcription-enhancing element in transgenic plant cell suspension culture, with induction occurring in response to the addition of an elicitor to the cell culture medium.

Where inhibition of gene expression is desired in a plant being invaded by a microbial pathogen, such as a phytopathogenic fungus, then either a portion or all of that coding sequence or cDNA sequence can be operably linked to a promoter functional in plant cells, but with the orientation of the coding sequence opposite to that of the promoter (i.e., in the antisense orientation) so that the transcribed RNA is complementary in sequence to the mRNA, and so that the expression of the antisense molecule is induced in response to pathogen invasion. In addition, there may be a transcriptional termination signal downstream of the nucleotides directing synthesis of the antisense RNA.

The present inventors have isolated a DNA sequence which mediates the inducible expression of a downstream gene in plant cells in response to invasion by a potential plant pathogen and/or treatment with an elicitor or other chemical signals. For example, a combination of ethylene and methyl jasmonate serve to induce downstream gene expression via the qualitative transcription regulatory sequence. It is understood that there may be a multiplicity of sequence motifs within that regulatory sequence, where individual motifs each respond to one or more distinct environmental signal. As specifically exemplified, this transcription-regulating sequence is derived from the EAS4 locus of *N. tabacum,* and it is given in SEQ ID NO:7. The deduced amino acid sequence for the EAS protein is given in SEQ ID NO:8. The open reading frame of the EAS4 gene, which is interrupted by six introns, is provided in SEQ ID NO:7.

A computer search for nucleotide sequence homology in sequences in Genbank to the SEQ ID NO:2 sequence revealed no known nucleotide sequences with significant homology, except for the CAAT and TATA transcriptional control sequences.

Organization of the EAS genes in the *N. tabacum* genome was described in Facchini and Chappell (1992) supra using an EAS probe and Southern hybridization experiments. Under conditions of high stringency, multiple fragments hybridized with analysis indicating that there is a gene family with some 12–16 members in the tobacco genome. In these experiments, however, the probe included the EAS coding sequence rather than the promoter and promoter-associated regulatory sequences.

EAS homologous genes can be identified and isolated from plant species other than *N. tabacum* based on significant degrees of nucleotide sequence homology; i.e., DNA:DNA hybridization under conditions of moderate to high stringency with a tobacco EAS coding sequence probe allows the identification of the corresponding gene from other plant species. A discussion of hybridization conditions can be found for example, in Hames and Higgins (1985) *Nucleic Acid Hybridization,* IRL Press, Oxford, U.K. Generally sequences which have at least about 70% nucleotide sequence homology can be identified by hybridization under conditions of moderate stringency. Under such conditions, it is generally preferred that a probe of at least 100 bases be used. Most preferably, in the present case, the probe will be derived from the coding portion of the EAS4 coding sequence. Labels for hybridization probes can include, but are not limited to, radioactive groups, fluorescent groups and ligands such as biotin to which specific binding partners (which are in turn labeled) bind. It is the label which allows detection of the hybridization probe to the target nucleic acid molecule. Alternatively, well-known and widely accessible polymerase chain reaction (PCR) technology is advantageously used to amplify sequences with significant nucleotide sequence homology to a target sequence.

It is understood that nucleic acid sequences other than the EAS coding sequence disclosed in SEQ ID NO:7 will function as coding sequences synonymous with the exemplified EAS4 coding sequence. Nucleic acid sequences are synonymous if the amino acid sequences encoded by those nucleic acid sequences are the same. The degeneracy of the genetic code is well-known to the art; i.e., for many amino acids, there is more than one nucleotide triplet which serves as the codon for the amino acid. It is also well-known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure,* Vol. 5, Suppl. 3, pp. 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Terpene cyclase genes can be found in solanaceous plants, including *N. tabacum* and *Hyoscyamus muticus,* as disclosed herein, and in members of the mint family (Labitaceae) and the Euphorbiaceae, including but not limited to those which have been demonstrated to contain sequences of significant homology, and in substantially all plants. Preferably, EAS4 homologs will be selected from the Solanaceae. Such sequences can be identified by nucleic acid hybridization experiments or when cloned in expression vectors, by cross reaction to tobacco EAS-specific antibody, or any other means known to the art, including the use of PCR technology carried out using oligonucleotides corresponding to portions of SEQ ID NO:7, preferably in the region encoding EAS. Antibody can be prepared after immunizing an experimental animal with EAS purified as described in Vogeli et al. (1990) *Plant Physiology* 93:182–187 or using a peptide conjugate, where the amino acid sequence of the peptide is taken from a hydrophilic portion of the EAS amino acid sequence (SEQ ID NO:8). Monoclonal and polyclonal antibody production techniques are readily accessible to the art (See, e.g., Campbell (1994) *Monoclonal Antibody Technology. Laboratory* Techniques in Biochemistry and Molecular Biology, Vol. 13, Burdon and Knippenberg, eds, Elsevier, Amsterdam; Harlow and Lane (1988) *Antibodies: A Laboratory Manual*, Cold Spring Harbor Laboratory, Cold Spring Harbor, N.Y.).

Alternately, a cDNA library (in an expression vector) can be screened with EAS-specific antibody, or EAS peptide-specific antibody can be prepared using peptide sequence(s) from hydrophilic regions of the EAS protein (SEQ ID NO:8) and technology well-known in the art.

An inducible transcription regulatory sequence can be operably linked to any promoter sequence functional in plants as understood by the skilled artisan; where a regulatory element is to be coupled to a promoter, generally a truncated (or minimal) promoter is used, for example, the truncated 35S promoter of Cauliflower Mosaic Virus, CaMV). Truncated versions of other constitutive promoters can also be used to provide CAAT and TATA-homologous regions; such promoter sequences can be derived from those of *A. tumefaciens* T-DNA genes such as nos, ocs and mas and plant virus genes such as the CaMV 19S gene. It will be understood that the goals of a skilled artisan will determine the choice of particular promoters used with the inducible transcription regulatory sequences. It is further understood that when a protein capable of generating a cell death response is to be expressed, then there is preferably no basal transcriptional (and translational) expression in the absence of inducer. The minimization of basal expression is less critical in applications for inducible gene expression where the gene product has no significant toxicity to the plant cells producing it.

A minimal promoter contains the DNA sequence signals necessary for RNA polymerase binding and initiation of transcription. For RNA polymerase II promoters, the promoter is identified by a TATA-homologous sequence motif about 20 to 50 bp upstream of the transcription start site and a CAAT-homologous sequence motif about 50 to 120 bp upstream of the transcription start site. By convention, the skilled artisan often numbers the nucleotides upstream of the transcription start with increasingly large numbers extending upstream of (in the 5' direction) from the start site. Generally, transcription directed by a minimal promoter is low and does not respond either positively or negatively to environmental or developmental signals in plant tissue. An exemplary minimal promoter suitable for use in plants is the truncated CaMV 35S promoter, which contains the regions from −90 to +8 of the 35S gene.

The inducible transcription regulatory sequence (qualitative transcription regulatory sequence) is localized to the region between −167 and −100 relative to the EAS4 transcription initiation site (nucleotides 406 to 473, initiation at nucleotide 573 in SEQ ID NO:2). It is understood that there may be a plurality of sequence motifs which respond to particular stimuli. Operably linking this sequence directly upstream of a minimal promoter functional in a plant cell confers inducible expression of a coding sequence operably fused just downstream of the promoter, e.g., a heterologous coding sequence, and the skilled artisan understands spacing requirements and other requirements for translational expression of the coding sequence. The heterologous coding sequence is preferably for an elicitin-like protein of a plant pathogenic microorganism (virus, bacterium or fungus), for example, the sequence encoding the parA1 gene product (elicitin) of *Phytophthora parasitica* where disease resistance via the hypersensitivity response to an invading potential plant pathogen is desirable. Harpin proteins of certain phytopathogenic bacteria also can serve as inducers of expression mediated by the EAS4-derived inducible transcriptional regulatory sequences. Inclusion of additional 5' flanking sequence from the EAS4 gene allows for increased levels of downstream gene expression. Preferred is the use of a sequence including the −266 to +1 region of EAS4 (nucleotides 307 to 573 of SEQ ID NO:2), and more preferred is the sequence including −567 to +1 (nucleotides ▲ to 573 of SEQ ID NO:2).

An alternative to the use of the fusion of the EAS4 transcription regulatory sequence fused to a heterologous minimal promoter is the use of the promoter region of EAS4 in conjunction with the upstream promoter-associated regulatory elements. In such an application the use of nucleotides 307 to 463, or more preferably for greater levels of downstream expression, nucleotides 371 to 463, 311 to 462, and 10 to 573 of SEQ ID NO:2.

In a plant such as *N. tabacum*, the instant inducible transcription regulatory element directs the induction of downstream gene expression in response to invading plant pathogens and certain compositions such as some fungal cellulases and certain plant and fungal cell wall fragments. Plant pathogens which can trigger this expression include, but are not limited to, Xanthomonas, *Pseudomonas syringae*, Phytophthora species including *parasitica*, and Peronospora species (e.g., *tabaci*).

Coding sequences suitable for expression in a plant are operably linked downstream of the regulated promoter construct. Transgenic plants can be constructed using the chimeric gene consisting essentially of the regulated promoter, any additional transcription-enhancing sequences, and the desired coding sequence including the necessary sequence signals for its translation. Where disease resistance is to be advantageously induced in response to invasion of a transgenic plant tissue by a potential plant pathogen or in response to treatment with an elicitor or other chemical signal which induces EAS4 gene expression, the coding sequence is preferably for an elicitin of a plant pathogenic microorganism, e.g., the parA1 gene product of *Phytophthora parasitica* (as described in Kamoun et al. (1993) supra). Other elicitin-like proteins have been described in the readily available scientific literature, and include those from Phytophthora species, Peronospora species, and Xanthomonas species, among others.

Alternative coding sequences which can be expressed under the regulatory control of the present inducible transcription regulatory element for improvement of the resistance of a (transgenic) plant or plant tissue exposed to a viral, bacterial or fungal plant pathogen include, but are not limited to, chitinase, TMV coat protein or other plant virus coat protein, NIa virus gene and others.

Additionally, or alternatively, induction of the regulated construct can be induced, for example, by treating the transgenic plant or tissue with an elicitor or with a bacterium, virus or fungus (preferably not pathogenic for the host plant) capable of inducing expression via the inducible transcription regulatory element of a coding sequence not capable of turning on the HR, or disease resistance directly could be achieved. Coding sequences which may be advantageously expressed include an insecticidal protein, such as one of the *Bacillus thuringiensis* crystal proteins, which when expressed would protect the plant from insect pests.

Phytoalexin synthesis from the native EAS4 gene, or induction of gene expression mediated by the present regulated EAS4 promoter or the inducible transcription regulatory element in combination with at least a heterologous minimal promoter, can be induced by treating the plant tissue or cells with a wide variety of defined chemicals, crude fungal culture filtrates, fungal cell wall extracts and oligosaccharides from plant or fungal cell walls [Albersheim and Valent (1978) *J. Cell. Biol.* 78:627–643]. Other compounds capable of inducing the HR include certain cellulases, for example, *Trichoderma reesei* or *Trichoderma viride* cellulases, and certain plant or fungal cell wall fragments, among others.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment (See Davey et al. (1989) *Plant Mol. Biol.* 13:275; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol. Biol.* 42:205; Gasser and Fraley (1989) *Sci.* 244:1293; Leemane (1993) *Bio/Technology.* 11:522; Beck et al. (1993) *Bio/Technology.* 11:1524; Koziel et al. (1993) *Bio/Technology,* 11:194; and Vasil et al. (1993) *Bio/Technology.* 11:1533.). Techniques are well-known to the art for the introduction of DNA into monocots as well as dicots, as are the techniques for culturing such plant tissues and regenerating those tissues. Monocots which have been successfully transformed and regenerated include wheat, corn, rye, rice and asparagus. For example, U.S. Pat. No. 5,350, 689 (1994, Shillito et al.) describes transgenic *Zea mays* plants regenerated from protoplasts and protoplast-derived cells. For efficient production of transgenic plants, it is desired that the plant tissue used for transformation possess a high capacity for regeneration. Transgenic aspen tissue has been prepared and transgenic plants have been regenerated [Devellard et al. (1992) *C.R. Acad. Sci. Ser. VIE* 314:291–298K; Nilsson et al. (1992) *Transgenic Res.* 1:209–220; Tsai et al. (1994) *Plant Cell Rep.* 14:94–97]. Poplars have also been transformed [Wilde et al. (1992) *Plant Physiol.* 98:114–120]. Technology is also available for the manipulation, transformation and regeneration of Gymnosperm plants in the laboratory. For example, U.S. Pat. No. 5,122,466 (1992, Stomp et al.) describes the ballistic transformation of conifers, with preferred target tissue being meristematic and cotyledon and hypocotyl tissues. U.S. Pat. No. 5,041,382 (1991, Gupta et al.) describes enrichment of conifer embryonal cells.

Techniques and agents for introducing and selecting for the presence of heterologous DNA in plant cells and/or tissue are well-known. Genetic markers allowing for the selection of heterologous DNA in plant cells are well-known, e.g., genes carrying resistance to an antibiotic such as kanamycin, hygromycin, gentamicin, or bleomycin. The marker allows for selection of successfully transformed plant cells growing in the medium containing the appropriate antibiotic because they will carry the corresponding resistance gene.

Other techniques for genetically engineering plant cells and/or tissue with an expression cassette comprising an inducible promoter or chimeric promoter fused to a heterologous coding sequence and a transcription termination sequence are to be introduced into the plant cell or tissue by Agrobacterium-mediated transformation, electroporation, microinjection, particle bombardment or other techniques known to the art. The expression cassette advantageously further contains a marker allowing selection of the heterologous DNA in the plant cell, e.g., a gene carrying resistance to an antibiotic such as kanamycin, hygromycin, gentamicin, or bleomycin.

The transcription regulatory sequences, particularly the inducible transcription regulatory element (or the EAS4 promoter with the inducible and preferably the transcription-enhancing element) is useful in controlling gene expression in transgenic plant cells in suspension cell culture as an alternative to expression in transgenic plants. For example, the EAS4 promoter including the transcription initiation signals, the inducible transcription regulatory element and the transcription-enhancing element, can be used to mediate the inducible expression of one or more heterologous coding sequence(s) in transgenic plant cells in suspension cell culture. When desired, expression of the coding sequence of interest is induced by the addition of an elicitor or other inducing chemical signal to the culture. Suspension culture cells respond to elicitors readily in comparison to intact plants. The heterologous coding sequence(s) can encode proteins which mediate synthesis of pharmaceutical compounds, poly-β-hydroxybutyrate synthesis or other secondary metabolites, cellulose, starch, sugars, oils, or the heterologous sequences can encode pharmaceutical proteins, insecticidal toxin proteins, antifungal proteins, antiviral proteins such as coat proteins to mediate resistance to virus infection, the N1a protein, chitinases, glucanases, male sterility proteins or sequences, proteins to improve nutritional quality or content, or developmental and/or tissue-specific programs or patterns. It is understood that transgenic plants can be similarly used to express heterologous coding sequences as can transgenic plant cells.

Where transgenic plants are to be induced for phytoalexin synthesis or for the expression of a heterologous coding sequence under the regulatory control of the EAS4 promoter or the inducible transcription regulatory element derived therefrom and/or the transcription-enhancing sequence derived from the EAS4 promoter as well, the elicitor must penetrate the cuticle of the plant to have an inductive effect. Alternatively, the plant tissue can be wounded to facilitate or allow the uptake of the elicitor into the plant tissue. A wide variety of inducing compositions, including elicitors and other chemical signals, such as the combination of ethylene and methyl jasmonate, can be effectively introduced into the transgenic plant suspension cell cultures, where there is significantly less of a barrier to the uptake and/or sensing of the elicitors. Where ethylene is used at a concentration between about 1 and about 50 ppm and the methyl jasmonate is used at a concentration between about 0.1 mM and about 1 mM.

The following examples use many techniques well-known and accessible to those skilled in the arts of molecular biology, in the manipulation of recombinant DNA in plant tissue and in the culture and regeneration of transgenic plants. Enzymes are obtained from commercial sources and are used according to the vendors' recommendations or other variations known to the art. Reagents, buffers and culture conditions are also known to the art. References providing standard molecular biological procedures include Sambrook et al. (1989) *Molecular Cloning,* second edition, Cold Spring Harbor Laboratory, Plainview; N.Y.; R. Wu (ed.) (1993) *Methods in Enzymology* 218; Wu et al. (eds.) *Methods in Enzymology* 100 and 101; Glover (ed.) (1985) *DNA Cloning,* Vols. I and II, IRL Press, Oxford, UK; and Hames and Higgins (eds.) (1985) *Nucleic Acid Hybridization,* IRL Press, Oxford, UK. References related to the manipulation and transformation of plant tissue include R. A. Dixon (ed.) (1985) *Plant Cell Culture: A Practical Approach,* IRL Press, Oxford, UK; Schuler and Zielinski (1989) *Methods in Plant Molecular Biology,* Academic Press, San Diego, Calif.; Weissbach and Weissbach (eds.) (1988) *Methods for Plant Molecular Biology,* Academic Press, San Diego, Calif.; I. Potrykus (1991) *Ann. Rev. Plant*

*Physiol. Plant Mol. Biol.* 42:205; Weising et al. (1988) *Annu. Rev. Genet.* 22:421; van Wordragen et al. (1992) *Plant Mol. Biol. Rep.* 19:12, Davey et al. (1989) *Plant Mol. Biol.* 13:273; Walden and Schell (1990) *Eur. J. Biochem.* 192:563; Joersbo and Brunstedt (1991) *Physiol. Plant.* 81:256 and other work cited in the foregoing references. Abbreviations and nomenclature, where employed, are deemed standard in the field and are commonly used in professional journals such as those cited herein.

All references cited in the present application are expressly incorporated by reference herein.

The following examples are provided for illustrative purposes and are not intended to limit the scope of the invention as claimed herein. Any variation in the exemplified compositions and methods which occur to the skilled artisan are intended to fall within the scope of the present invention.

EXAMPLES

Example 1

EAS-Specific Antibodies

Monoclonal and polyclonal antibodies specific for tobacco EAS were prepared as described by Vogeli et al. (1990) *Plant Physiology* 93:182–187. Additional antibody preparations could be made as polyclonal antibodies using purified EAS as antigen or using a peptide sequence conjugated to a carrier protein using well-known techniques. The amino acid sequence of a peptide for antibody production is selected from a particularly hydrophilic region of the protein (For antibody production technique, see, for example, Campbell (1994) *Monoclonal Antibody Technology, Laboratory Techniques in Biochemistry and Molecular Biology*, Vol. 13, Burdon and Knippenberg, eds, Elsevier, Amsterdam; Harlow and Lane (1988) *Antibodies: A Laboratory Manual*, Cold Spring Harbor Laboratory, Cold Spring Harbor, N.Y.).

Example 2

DNA and Protein Sequence Determination

Sequence determinations of single-stranded and double-stranded DNAs were carried out by the dideoxynucleotide chain termination procedure [Sanger et al. (1977) *Proc. Natl. Acad. Sci. USA* 74:8073–8077], with a Sequenase kit from United States Biochemical Corp., Cleveland, Ohio) or an automated fluorescence-based system (Applied Biosystems, Foster City, Calif.).

Example 3

Construction of a Full-Length EAS Clone

*Nicotiana tabacum* L. cv. KY14 cell suspension cultures were treated with *Trichoderma viride* cellulase (Type RS, Onozuka) at a final concentration 0.5 μg/ml during rapid growth phase to induce the expression of EAS. Parallel suspension cell cultures which did not receive cellulase served as controls. Cells were collected by gentle vacuum filtration 4 hrs after the addition of the cellulase elicitor to the induced culture.

A cDNA library was prepared in pcDNAII (Invitrogen, San Diego, Calif.) from polyA$^+$ RNA extracted from the *N. tabacum* cells treated for 4 hrs with elicitor. The library was screened by differential hybridization using polyA+ RNA prepared from the induced and control culture. Clones appearing to be positive were further screened by hybrid selection-in vitro translation-immunoprecipitation analysis as described by Alwine et al. (1979) *Methods Enzymol.* 68:220–242.

A putative positive EAS cDNA clone was used as a hybridization probe for the isolation of additional cDNA and genomic clones. The genomic library thus screened was one constructed in λEMBL3 using MboI partially digested DNA prepared from *N. tabacum* L. cv. NK326 hypocotyl DNA (Clontech, Palo Alto, Calif.). This screening yielded 8 independent clones, each of which appeared to represent a different chromosomal locus. EAS4 and EAS3 genomic clones were described in Facchini and Chappell (1992) supra, but are now known to have been incomplete.

Facchini and Chappell (1992) supra had misidentified the translation start sites of the EAS3 and EAS4 coding sequences in the genomic clone described therein. The correct translation start site for the EAS3 and EAS4 coding sequences have been determined to be methionine codons 165 bp upstream of the ATG codons previously identified as start sites. The corrected start site for EAS4 was mapped using a combination of primer extension assays to identify the transcription start site and additional N-terminal amino acid sequencing data of purified enzyme as noted hereinabove.

An amplimer of 110 bp was prepared by a polymerase chain reaction to provide a DNA sequence corresponding amino acids 56–92 of the EAS4 protein (see SEQ ID NO:12) and Facchini and Chappell (1992) supra. This amplimer was used as a hybridization probe to screen a cDNA library in pcDNAII (Invitrogen, San Diego, Calif.) prepared from polyA+ RNA from tobacco cell culture cells 4 hr after elicitor treatment (*Trichoderma reesei* cellulase). This amplimer was made using a sense primer (ATGCTGTTAGCAACCGGAAGG; SEQ ID NO:3) and a reverse primer (ATCCAAAATCTCATCAATTTC; SEQ ID NO:4), and the genomic EAS4 template in a standard PCR reaction [Saiki et al. (1988) *Science* 239:487–491]. The 110 bp amplimer was isolated after polyacrylamide gel electrophoresis using DE-81 paper (Whatman International, Inc., Clifton, N.J.). The isolated fragment was then radiolabeled with [α-$^{32}$P]-dCTP using a random priming kit from Stratagene (La Jolla, Calif.) for use as a hybridization probe in colony lifts of the cDNA library as previously described [Hanahan and Meselson (1980) *Gene* 10:63–67]. The longest clone obtained in these experiments appeared to lack 80 bp of 5' coding sequence.

To obtain a full-length clone, a RT/PCR approach was used. First strand cDNA was prepared from polyA+ RNA prepared from tobacco cells after induction with elicitor as described [Facchini and Chappell (1992) supra] using reverse primer having the sequence ATGAGTCCTTACAT-GTGA (SEQ ID NO:5). This sequence corresponds to nucleotides 459–477 downstream of the translation start site. The reverse transcriptase reaction was carried out in a 10 μl reaction (1 μg polyA+ RNA, 25 pmol reverse primer, 10 mM DTT, 2.5 mM each dATP, dGTP, dCTP, dTTP, 8 units RNase Block I (Stratagene, La Jolla, Calif.), first strand synthesis buffer used according to the manufacturer's instructions (Stratagene) for 1 hr at 37° C. This reaction was terminated by treating at 99° C. for 5 min. Then 40 μl of master PCR mix was added to the first strand reaction; PCR master mix contains 10 mM Tris-HCl pH 8.3, 50 mM KCl, 1.5 mM MgCl$_2$, 0.01% Tween-20, 0.01% (w/v) gelatin, 0.01% NP-40, 2.5 mM each deoxynucleotide triphosphate, 1 unit of TaqI polymerase, and 25 pmol forward primer (GGGAGC TC<u>GAATTCCATGG</u> CCTCAGCAGCAGCAGTTGCAAA CTAT, SEQ ID NO:6, EcoRI and NcoI recognition sites underlined and ATG translation start site in bold). PCR was carried out under standard conditions [Back et al. (1994) *Arch. Biochem. Biophys.* 315:523–532]

The 492 bp reaction product was digested with EcoRI and HindIII and subcloned into similarly cut pBluescript SK (Stratagene). A HindIII/XhoI fragment from another partial cDNA clone was subsequently cloned into the corresponding sites of the 5'-terminal sequence clone to generate a full-length cDNA clone named pBSK-TEAS. pBSK-TEAS DNA was transformed into *Escherichia coli* TB1 using a CaCl$_2$ protocol [Sambrook et al. (1989) supra]. Determination of the DNA sequence of the insert confirmed that this plasmid had the expected and desired structure (dideoxynucleotide chain termination procedure, United States Biochemical Corp., Cleveland, Ohio).

Example 4

Identification of EAS Homologous Sequences

Tobacco leaf genomic DNA was isolated as described in Murray and Thompson (1980) *Nucleic Acids Research* 8:4321–4325. After digestion of aliquots with desired restriction enzymes, the digested DNA samples were electrophoresed on 0.8% agarose gels and the size-separated DNAs were transferred to nylon membranes. DNA blots were hybridized with random primer radiolabeled cEAS1, which is truncated at the 5' end of the coding region, (prepared as in Sambrook et al. (1989) supra) at 60° C. in 0.25 M sodium phosphate buffer, pH 8.0, 0.7% SDS, 1% bovine serum albumin, 1 mM EDTA. The blot was then washed twice at 45° C. with 2× SSC, 0.1% SDS and twice with 0.2× SSC, 0.1% SDS (1× SSC is 0.15 M NaCl, 0.015 M sodium citrate, pH 7.0). Relative hybridization levels were estimated from autoradiograms using a video densitometer (MilliGen/Biosearch, Ann Arbor, Mich.).

Facchini and Chappell (1992) supra reported that Southern hybridization results indicated that there were 12–16 copies of EAS-homologs in the *N. tabacum* genome. To address the presence of significantly homologous sequences to tobacco EAS and apparent number of copies per genome of those sequences, Southern hybridization experiments are carried out using DNA isolated from other plant species.

Restriction endonuclease-digested genomic DNAs are separated by agarose gel electrophoresis (0.8% agarose), and then transferred to a Hybond-N$^+$ membrane (Amersham Corp., Arlington Heights, Ill.). Radiolabeled probe comprising coding sequences of EAS, and hybridizations are carried out essentially as described in Sambrook et al. (1989) supra. Moderate stringency conditions are used (hybridization in 4× SSC, at 65° C.; last wash in 1× SSC, at 65° C.).

Alternatively, PCR can be carried out using target DNA as template and primers derived from the EAS4 coding sequence in highly conserved regions (see SEQ ID NO:7) using well-known techniques.

Example 5

Detection of EAS Protein

The enzymatic activity of an expression product can be confirmed using the techniques described in Facchini and Chappell (1992) supra and in Back et al. (1994) *Arch. Biochem. Biophys.* 315:527–532.

For detecting the presence of EAS cross-reacting protein material, total protein fractions are prepared from 100 µl aliquots of bacterial culture harvested and concentrated by centrifugation for 2 min in a microfuge. After discarding the culture supernatant, cell pellets are resuspended in 100 µl 50 mM Tris-HCl, pH 6.8, 10 mM dithiothreitol, 2% sodium dodecyl sulfate, 0.01% bromophenol blue, 10% glycerol. For immunological detection 15 µl aliquots are electrophoresed over 11.5% SDS-polyacrylamide gels; for Coomassie blue-staining of the proteins, 35 µl aliquots are similarly electrophoresed. For soluble protein samples, the cells are processed as in the procedure for determination of enzymatic activity (see Back et al. (1995) supra or Facchini and Chappell (1992) supra). For immunological detection 10 µl aliquots are electrophoresed as above; for Coomassie blue-staining, 10–50 µl aliquots were electrophoresed.

After electrophoresis the proteins are stained with Coomassie blue, or the proteins are transferred to nitrocellulose membranes as described [Towbin and Gordon (1984) *Journal of Immunological Methods* 72:313–340] for immunodetection. After incubating for 30 min in 5% low-fat milk in 1× TBS (20 mM Tris-HCl, pH 7.5, 500 mM NaCl), the nitrocellulose blots were incubated overnight in the same solution containing monoclonal antibody specific for tobacco EAS (1:1000 dilution; Vogeli et al. (1990) *Plant Physiology* 93:182–187). Goat anti-mouse antibodies linked to alkaline phosphatase and the specific chromogenic dye were then incubated to visualize the binding of the EAS-specific antibody to the proteins immobilized on the nitrocellulose membranes [Leary et al. (1983) *Proc. Natl. Acad. Sci. USA* 80:4045–4049].

Example 6

Genomic EAS4 Clone

The 5'-truncated cDNA clone cEAS1 described in Facchini and Chappell (1992) supra was used as a hybridization probe for screening a *N. tabacum* cv. NK326 genomic library in the λEMBL3 vector (Clontech, Palo Alto, Calif.). DNA sequences were determined using routine subcloning and DNA sequencing protocols.

The DNA and deduced amino acid sequences of the EAS4 genomic clone are presented in SEQ ID NO: 7–8.

Example 7

Generation of Transgenic Plants

For studies of the function of portions of the upstream untranslated region of the EAS4 gene, HindIII/BamHI-ended fragments of this upstream DNA were cloned into pBI101 (Clontech, Palo Alto, Calif.) so that expression of the β-glucuronidase (GUS) reporter gene could be monitored in transformed plant cells. The 5'-flanking sequence of the EAS3 gene is given in SEQ ID NO:1 and the 5'-flanking sequence of the EAS4 gene is given in SEQ ID NO:2. In each of these sequences, the translation start site (ATG) is the last three nucleotides. By primer extension techniques, the EAS4 transcription start site was estimated at nucleotide 573 in SEQ ID NO:2. CAAT and TATA box motifs are identified at nucleotides 429 to 432 and at nucleotides 456 to 459 in SEQ ID NO:1 (EAS3) and at nucleotides 513 to 516 and at nucleotides 540 to 543 in SEQ ID NO:2 (EAS4).

The transformed plant cell lines were produced using a modified *Agrobacterium tumefaciens* transformation protocol. The recombinant plasmids containing the sequences to be introduced into plant tissue were transferred into *A. tumefaciens* strain GV3850, by triparental mating with *E. coli* TB1 (pRK2013). *N. tabacum* leaves at a variety of stages of growth were cut into 1 cm$^2$ pieces, and dipped in a suspension of agrobacterial cells (about $10^4$ to $10$ cells/ml). After 3 to 10 minutes, the leaf segments were then washed in sterile water to remove excess bacterial cells and to reduce problems with excess bacterial growth on the treated leaf segments. After a short drying time (30 to 60 seconds), the treated leaf segments are placed on the surface of Plant Tissue Culture Medium without antibiotics to promote tissue infection and DNA transfer from the bacteria to the plant tissue. Plant Tissue Culture Medium contains per liter: 4.31 g Murashige and Skoog Basal Salts Mixture (Sigma Chemical Company, St. Louis, Mo.), 2.5 mg benzylaminopurine (dissolved in 1 N NaOH), 10 ml of 0.1 mg/ml indoleacetic acid solution, 30 g sucrose, 2 ml Gamborg's Vitamin Solution (Sigma Chemical Co., St. Louis, Mo.) and 8 g agar. The pH is adjusted between pH 5.5 and 5.9 with NaOH. After 2 days, the leaf segments were transferred to Plant Tissue Culture Medium containing 300 $\mu$g/ml kanamycin, 500 $\mu$g/ml mefoxin (Merck, Rahway, N.J.). The kanamycin selects for transformed plant tissue, and the mefoxin selects against the agrobacterial cells.

It is necessary to minimize the exposure of the explant tissue to agrobacterial cells during the transformation procedure in order to limit the possible induction of the regulated parA1 coding sequence during the production of the transgenic plant cells, which would cause a cell death response. Accordingly, the ballistic technique for the introduction of heterologous DNA containing cell suicide genes under the regulatory control of the inducible transcriptional regulatory element is a useful alternative transformation technique because it does not entail the use of agrobacterial cells or fungal cell wall digestive enzymes (as necessary for the generation of protoplasts for electroporation), both of which lead to induction of the coding sequences under the control of that regulatory element.

Transgenic plants were regenerated essentially as described by Horsch et al. (1985) *Science* 227:1229–1231.

The resulting transgenic plants were tested for the expression of the $\beta$-glucuronidase (GUS) reporter gene using 5-bromo-4-chloro-3-indolyl-$\beta$-D-glucuronic acid as described by Jefferson et al. (1987) *EMBO Journal* 6:3901–3907, using untreated (control) conditions and inducing conditions. An inducing condition is the intercellular application of *T. viride* cellulase to tobacco tissue in the transgenic plants (using a mechanical pipetter to apply 50–100 $\mu$l inducing composition to interstitial tissue); controls were mock-applied but not treated with cellulase elicitor. Tobacco tissue was wounded with a scalpel in some experiments to facilitate exposure to the inducing compounds.

Example 8

Deletion Analysis of Promoter and Promoter-Associated Region

In separate reactions, the EAS4-derived DNA sequence encompassed by –567 to +67 relative to the transcription start site (nucleotides 6 to 642, SEQ ID NO:2, EAS4) was substituted for the Cauliflower Mosaic Virus (CaMV) 35S promoter [Benfey et al. (1990) *EMBO Journal* 9:1677–1684] in the GUS-reporter vector pBI221 (Clontech, Palo Alto, Calif.). Deletion mutants in the EAS4 upstream regions were then isolated after restriction endonuclease cutting and Bal31 digestion. Analysis of the cEAS promoter-GUS constructs was carried out in electroporated tobacco cell protoplasts and in stably transformed tobacco lines. Preliminary data for the transient expression demonstrated that SEQ ID NO:1 and SEQ ID NO:2 functioned in regulated gene expression.

The transient expression data obtained with the *N. tabacum* protoplasts into which various EAS3 and EAS4 promoter-GUS constructs were introduced are given in FIG. 1. Progressive deletions from the 5' end of the EAS4 promoter regions reduce the levels of expression, but inducibility is maintained for the –262, –202 and –110 constructs (relative to the transcription start site at nucleotide 573 of SEQ ID NO:2). The data indicate that only very low levels of GUS are expressed via either EAS3 promoter region construct. Similarly, the truncated CaMV 35S promoter alone is not induced by the elicitor treatment, which provides induction via the inducible transcription regulatory element of EAS4.

Figure 2A:
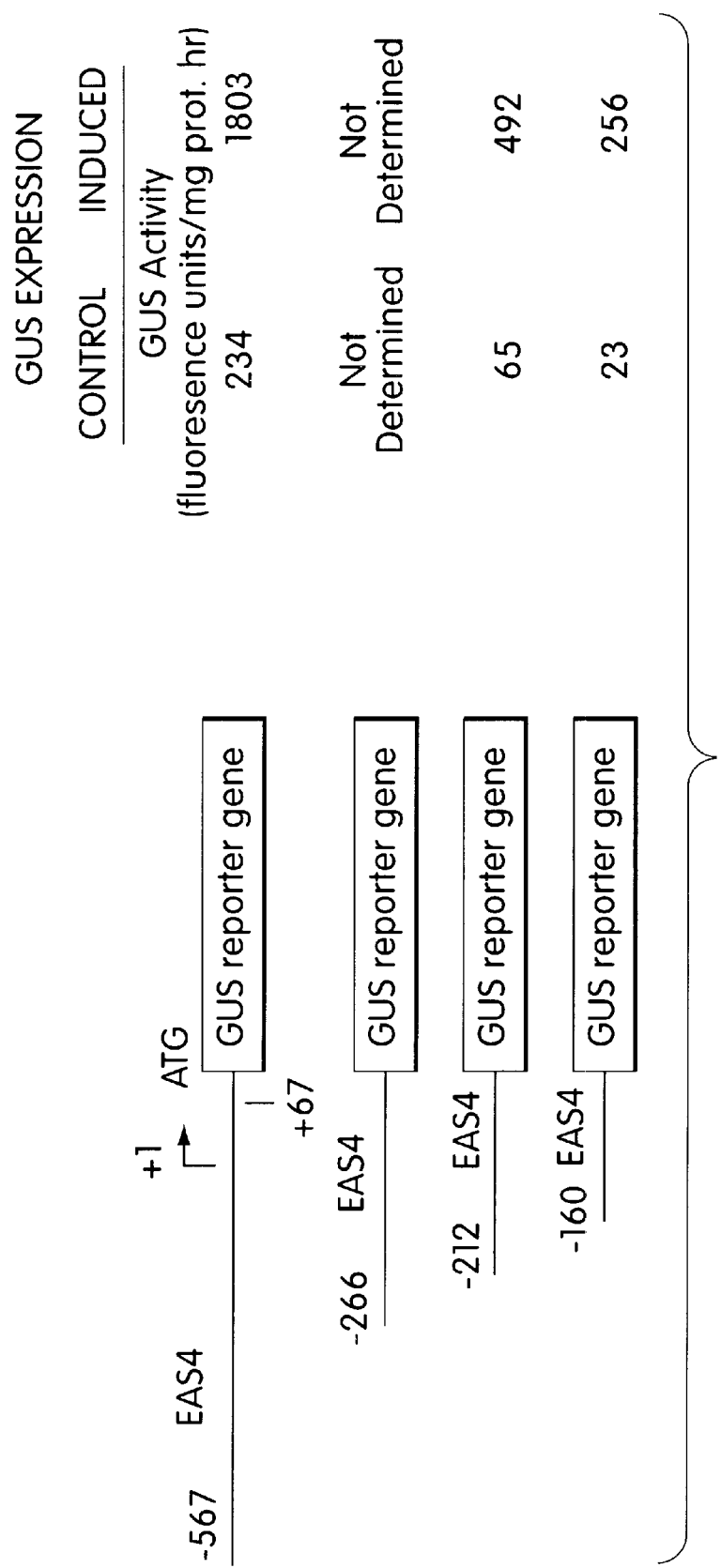
Figure 2B:
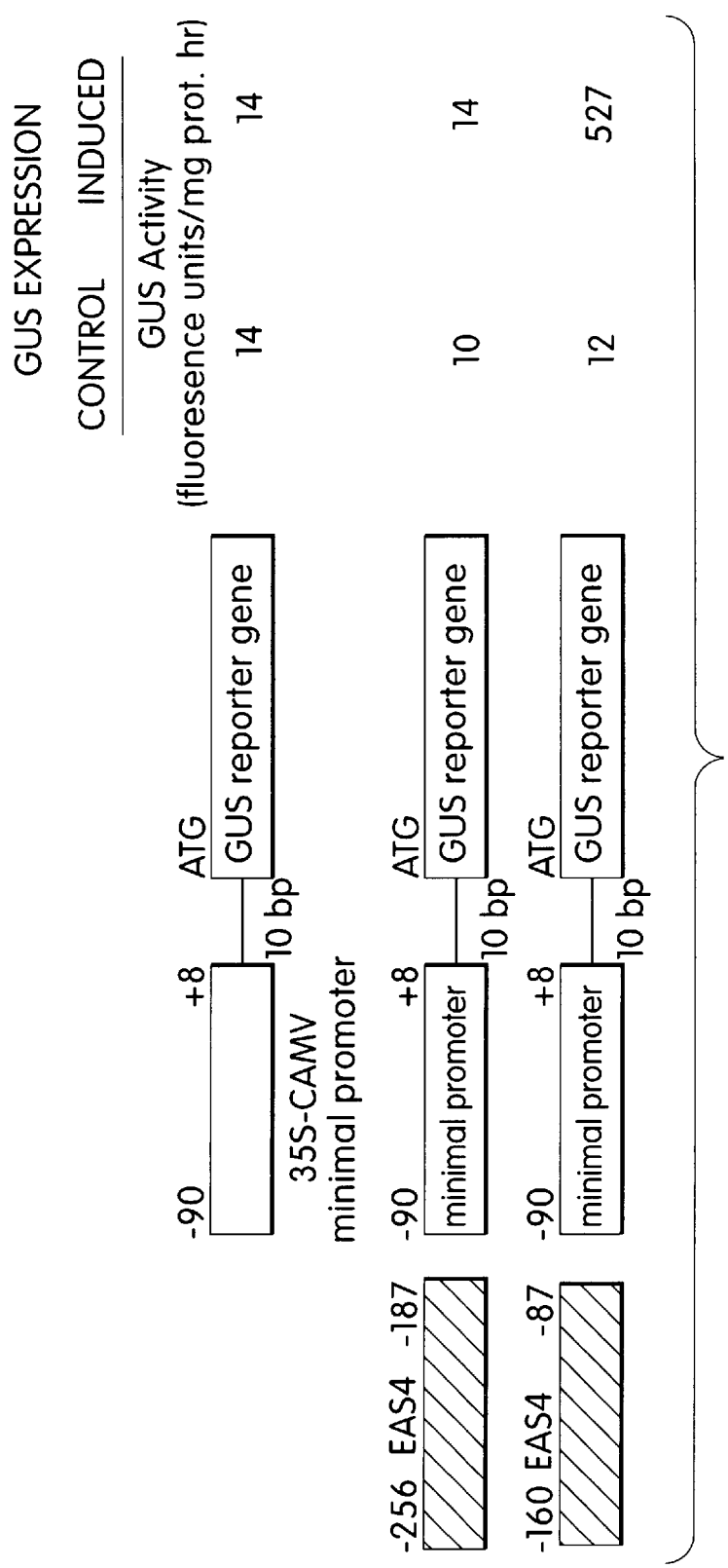
Figure 3:
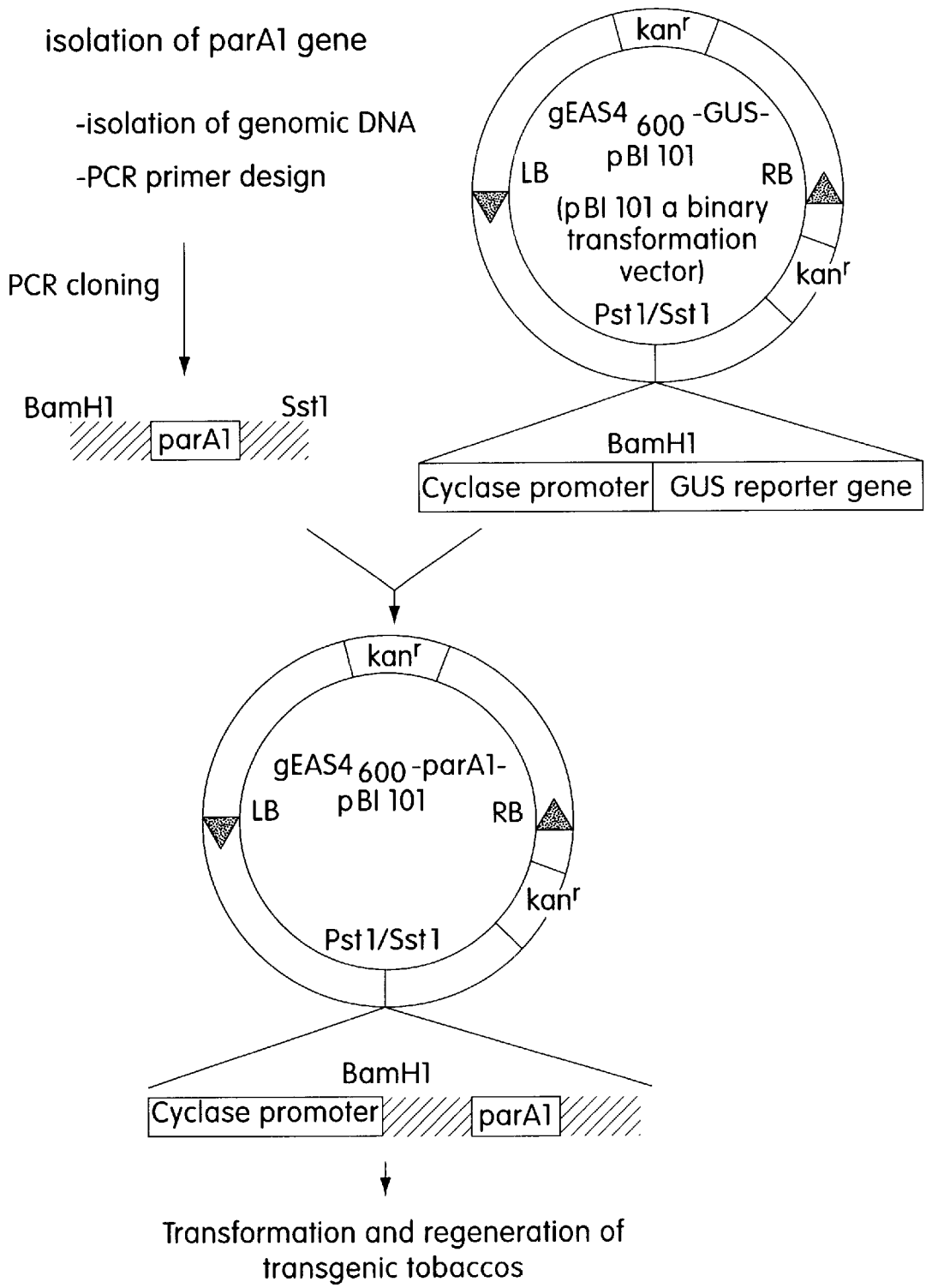

The data in FIGS. 2A–2B indicate that deletion of genetic material between –567 and –160 reduce the level of downstream gene expression but does not destroy the inducibility of expression. Therefore, the DNA sequences between –567 and –160 appear to contain transcription-enhancing activity. Most of the transcription-increasing activity appears to reside between –567 and –212, but additional enhancement appears to be mediated by sequence information between –212 and –160 relative to the transcription start site (transcription start site is nucleotide 573; –567 is nucleotide 1, –212 is nucleotide 361, and –160 is nucleotide 413, all in SEQ ID NO:2).

In the Gain of Function assay data in FIG. 2B, the DNA sequence information necessary to mediate induction in response to elicitor treatment is located between –160 and –87 relative to the EAS4 transcription start site (i.e., between nucleotides 413 and 486 of SEQ ID NO:2). In these experiments the EAS-derived sequences were placed in front of a truncated CaMV 35S promoter [Benfey et al. (1990) *EMBO J.* 9:1677–1684]. This figure also demonstrates that the EAS4-derived transcription regulatory region functions when fused to a heterologous minimal promoter.

In other experiments, either the entire –567 to +67 EAS4 upstream region or 5' deletions thereof were inserted upstream of the GUS ($\beta$-glucuronidase) reporter gene in vector pBI101 (Clontech, Palo Alto, Calif.), and expression levels of the GUS reporter were assayed under inducing and noninducing conditions. 160 bp upstream of the transcription start site of EAS4 were sufficient to direct the regulated expression of the GUS reporter gene, although the presence of additional upstream sequences mediated increased expression.

Constructs containing a minimum of 167 bp upstream of the EAS4 transcription start site gave transient gene expression in electroporated protoplasts and confer elicitor-inducibility of GUS reporter gene expression (minimum of 2.5-fold increase in gene expression). By contrast, the EAS3 upstream region (SEQ ID NO:1) does not appear to support high levels of reporter gene expression in the transient expression system, nor does it appear to confer elicitor-inducibility to the downstream reporter gene.

In part, the elicitor-inducible GUS reporter gene expression was expected in the protoplast system because those protoplasts were generated using fungal cell wall digestive enzymes, and those enzymes have been shown to elicit phytoalexin production and sesquiterpene cyclase gene expression in plants [Chappell et al. (1991) *Plant Physiology* 97:693–698]. A possible explanation is that the 6 hr time period before the experiment allows the cells to return to an elicitor-responsive state.

PBI101 is commercially available from Clontech (Palo Alto, Calif.). It contains the CaMV 35S promoter upstream of the GUS reporter gene in a pUC19 vector; thus it serves as a vector for transient expression experiments where the recombinant vector is introduced into plant protoplasts. The presence of this plasmid and its derivatives is selected by growth on kanamycin. A "promoter-less" GUS cassette in the Agrobacterium binary plasmid vector pBIN19 (Bevan, M. (1994) *Nucl. Acids Res.* 12:8711) similarly carries a plant-expressible kanamycin resistance determinant.

Example 9

Identification of Inducible Transcription Regulatory Element

The 5' flanking domains of genomic EAS3 and EAS4 clones were mapped by S1 nuclease protection and primer extension experiments [Sambrook et al. (1989) supra]. Subclones comprising up to 1 kb 5' to the translation start site were sequenced and fused to the β-glucuronidase (GUS) reporter gene in PBI101 for studies in transgenic plant tissue. The resulting recombinant plasmids were then electroporated into tobacco protoplasts. GUS activity was measured in transient expression assays, and stable transformed tobacco cell lines were also isolated for studies of GUS induction and expression.

Constructs were prepared containing a minimum of about 200 bp of nucleotide sequence upstream of the EAS4 transcription start site in the modified pBI101 vector, and a β-glucuronidase (GUS) reporter gene were made and analyzed for ability to drive regulated GUS expression. 200 bp of flanking sequence appeared sufficient to drive transient gene expression in electroporated protoplasts and confers elicitor inducibility to GUS expression (minimum of 2.5 fold induction). Similar experiments with the EAS3 flanking sequence indicated that 200 bp from the EAS3 locus did not support either high levels of GUS expression or elicitor responsiveness in transformed plant cells. Cellulase and elicitins from Phytophthora [Ricci et al. (1989) *Eur. J. Biochem.* 183:555–563] serve to induce gene expression mediated by the EAS4-derived regulatory sequences.

Further studies related to the identification of sequences important in mediating induced gene expression in response to pathogen invasion, as modeled using cellulase or elicitins, were carried out after oligonucleotide site-directed mutagenesis [Kunkel (1985) *Proc. Natl. Acad. Sci. USA* 82:488–492] of the putative regulatory region of EAS4. Substitution of GT for the wild-type CA at −233 and −234 relative to the EAS4 transcription start site (nucleotides 334–335 of SEQ ID NO:2) did not appear to alter the expression of the GUS reporter gene as measured after incubation in the presence of elicitor (cellulase) for 20 hours.

Preliminary methylation interference and gel retardation studies carried out essentially as described [Sambrook et al. (1989) supra] indicated that an octameric sequence centered around −233 relative to the translation start site (centered around 334 of SEQ ID NO:2) binds proteins from plant cell nuclei. Methylation interference data suggested that the G at position −233 was preferentially protected against methylation by DMS (dimethyl sulfate) if first allowed to interact with nuclear extracts. The results of gel retardation studies were consistent with those obtained in the methylation protection experiments. When DNA fragments containing the −343 to −140 region (relative to the translation start site) (nucleotides 230 to 433 of SEQ ID NO:2) were examined after reaction to nuclear extracts, mobility in native acrylamide gel electrophoresis appeared retarded. Protein binding was abolished by the GT to CA substitution at positions −234 and −233. Similar results were observed in control and elicitor-induced cell extracts, and reporter gene expression was not changed by this 2 bp mutation. Thus, it is concluded that the region around −233 is not directly involved in the induction of gene expression in response to pathogen invasion or elicitor treatment.

Preliminary experiments indicate that EAS4 DNA sequences between −253 and −48 relative to the EAS4 transcription start site (between nucleotides 320 and 525 of SEQ ID NO:2) have qualitative and quantitative effects on downstream reporter gene expression. Sequences between −110 and −1 of EAS4 relative to the transcription start site of EAS4 (nucleotides 463 to 572 of SEQ ID NO:2) to mediate the inducible response, while sequences between −202 and −110 relative to the EAS4 transcription start site (nucleotides 371 to 463 of SEQ ID NO:2) enhance the levels of both induced and uninduced reporter gene expression.

Example 10

Disease-resistant Transgenic Plants

The parA1 coding sequence was isolated from *Phytophtora parasitica* race O as follows: Genomic DNA was isolated and used as template in PCR with a SIG forward primer (CGTTGGATCCCCACCTCATCCGAAATGAAC; SEQ ID NO:9; BamHI site underlined; nucleotides 25–27 correspond to the translation start site and reverse primer (GGCTGAGCTCCTGGACGFCAGAGATCAAACC; SEQ ID NO:10; SstI site underlined) to amplify the coding region of the ParA1 elicitin including the signal peptide coding sequence. To isolate an amplimer corresponding to the coding sequence of the ParA1 elicitin, the MAT forward primer (GCCGGATCCTTAGTACTAGTTGCACCACCACGCAGCAAACTG, SEQ ID NO:11; BamHI site, GGATCC, and SpeI site, ACTAGT, underlined; translation start site at nucleotides 12–14 and the reverse primer as before (SEQ ID NO:10) were used with genomic DNA as template. The amplimer sequences of the elicitin-with-signal peptide and the nature elicitin are given in SEQ ID NO:15 and SEQ ID NO:17, respectively.

For subcloning into pBluescript (Stratagene, La Jolla, Calif.) or into pEAS4 constructs, the amplimer DNA was digested with BamHI and SstI. Where the mature protein's coding sequence is used, the mature elicitin/pEAS4 construct can be digested with SpeI to insert a plant signal sequence at the 5' end of the open reading frame. The pEAS4-GUS vector is digested with BamHI and SstI, with the large fragment of DNA being purified after agarose gel electrophoresis.

FIG. 3 illustrates the molecular manipulations leading to the generation of disease-resistant plants. The coding sequence for the ParA1 elicitin is isolated by PCR so as to have BamHI and SstI ends. gEAS4$_{600}$ -GUS-pBI101, which directs the expression of the GUS reporter gene under the regulatory control of the EAS promoter, is digested with BamHI and SstI to release the GUS reporter gene. Then the BamHI/SstI-digested ParA1 amplimer is ligated to the large fragment produced after digestion of gEAS4$_{600}$ -GUS-pBI101 to produce gEAS4$_{600}$-parA1-pBI101, from which the ParA1 elicitin is synthesized after induction with a suitable elicitor once plant cells or tissue have been transformed.

While various embodiments of the present invention have been described in detail, it is apparent that modifications, extensions, adaptations and optimizations may occur in those skilled in the art. It is to be expressly understood that such modifications and adaptations and so on are within the spirit and scope of the present invention, as set forth in the claims.

What is claimed is:

1. A plant or plant cell genetically engineered to contain a chimeric gene comprising, in operable linkage from 5' to 3', (i) a pathogen- or elicitor-inducible transcription regulatory element, wherein said pathogen- or elicitor-inducible transcription regulatory element is selected from the group consisting of (1) a pathogen- or elicitor-inducible transcription regulatory element comprising the nucleotide sequence shown in SEQ ID NO:2 from the nucleotide 458 to nucleotide 473; (2) a pathogen- or elicitor-inducible transcription regulatory element comprising the nucleotide sequence shown in SEQ ID NO:2 from nucleotide 406 to nucleotide 473; and (3) a pathogen- or elicitor-inducible transcription regulatory element comprising the nucleotide sequence shown in SEQ ID NO:2) from nucleotide 371 to nucleotide 473, (ii) a promoter functional in a plant, and (iii) a coding sequence, wherein said promoter and said coding sequence are not naturally associated with said inducible transcription regulatory element, and wherein said coding sequence is expressed under the regulatory control of said inducible transcription regulatory element.

2. The plant or plant cell of claim 1, wherein said pathogen- or elicitor-inducible transcription regulatory element comprises the nucleotide sequence shown in SEQ ID NO:2 from nucleotide 458 to nucleotide 473.

3. The plant or plant cell of claim 1, wherein said pathogen- or elicitor-inducible transcription regulatory element comprises the nucleotide sequence shown in SEQ ID NO:2 from nucleotide 406 to nucleotide 473.

4. The plant or plant cell of claim 1, wherein said pathogen- or elicitor-inducible transcription regulatory element comprises the nucleotide sequence shown in SEQ ID NO:2 from nucleotide 371 to nucleotide 473.

5. The plant or plant cell of claim 1, wherein said promoter functional in a plant is the Cauliflower Mosaic Virus 35S gene minimal promoter.

6. The plant of claim 1, wherein said plant is a dicotyledonous plant.

7. The plant of claim 6, wherein said dicotyledonous plant is a member of the Solanaceae.

8. The plant of claim 7, wherein said plant is *Nicotiana tabacum*.

9. The plant of claim 1, wherein said plant is a monocotyledonous plant.

10. The plant of claim 1, wherein said plant is a gymnosperm.

11. The plant of claim 10, wherein said plant is a member of the Coniferae.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
       (A) LENGTH: 512 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Nicotiana tabacum (xi) SEQUENCE DESCRIPTION: SEQ ID NO:1:

```
CCGCGATTGG AGGATGTTGT ACGTCGAGCT ACGCGGCACC GCGCTTAATT TTACTCGGTC      60
AAGAAGGAAC GGGGATGGTG GTCAACGAAA CACGACGGGC CCGACATCAT GCCTGACAAC     120
CCGCCGTGGG TGAAGAAGTC GACGTTGGAA AAGAGCTACA GCCTGCTCCA CGCGGATGCG     180
GGGATGGCCG CTGACTACAG AAAGTGCGTT TCCCGCCACC CGGGGCGAGC CCGGGTTTTG     240
AAGATCAATG CTGACCGAAC CAGACGGCGG TACGTCATCC GCTTGAGGGT AGAGACGGAT     300
CAGTTCTTGT TGTCGTGTGT CGAACTCGGG ACGTTTGTCA CATGGCTGGA CGGGTTATTC     360
GCCGCCATCA ACGTGTCGCC GCCAATCGAC GAGCGCGACT TTCCCAGAGA CTTTAGCGTG     420
CCACGGATCA ATTACATTAA CTAGTCTCTC ACCACTATAT ATACTTGTCC CTTCTCTTCC     480
ATTTAAGTAG AGTTCCTTTC TTTCTTCCTT AA                                   512
```

(2) INFORMATION FOR SEQ ID NO:2:

(i) SEQUENCE CHARACTERISTICS:
       (A) LENGTH: 642 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Nicotiana tabacum (xi) SEQUENCE DESCRIPTION: SEQ ID NO:2:

```
TAGGTGAATG TCAGGGCTTA TGCTCCACGA TACTTATGCC CTGCCAGTAC ACCTCGCGGT      60
GGGACTCGCT CAAAAAACGT CTTTGTTGTG AGAAATTGCA ATTTTGAACC TCTACAATTT     120
CGACAAAACC TTGGTTCGTG AAAACTGTTT GATTAACTTT TAGACCATCC AGTCAATTTA     180
ACTCTAAACT GACCTAAATA AATACTACGT ACACTAGTCT TTAAGTTCAT CAAAGTGGAC     240
TCTGCATTAA TAATTGAAAT TTATGCCGCA ACAATGACAT TAGGTTTTAT AAATAAAGTA     300
ATAGGAATTT GATAGTTCCA GGAAACAACT CTACAGTACT CCCTTATTTT GTGCCTTTTT     360
AAATAATATT ATTCAGTTGA CGAAACAAAT AAATAAAATA TTTGGGAAAC TGGATCAATA     420
```

-continued

```
GACCCCAGAC GCCAACAATG AATCAAAAGG CTGCTAGCTA GTGTAAAGTC TAGTAAGGCA      480

ACTGGGAAAT TAAATGATTA GGTGCTTTTG ATCAATTACA TTAACTAGTC TCTCACCACT      540

ATATATACTT GTCCCTTCTC TTCCATTTAA GTAGAGTTCC TTTCTTTCTT CCTTAAAACT      600

TAAAAGAACA AGTAAAAATA CACTCATCTT TAATTAGCAA TG                        642
```

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR"

(iii) HYPOTHETICAL: NO (iv) ANTI-SENSE: NO (xi) SEQUENCE DESCRIPTION: SEQ ID NO:3:

```
ATGCTGTTAG CAACCGGAAG G                                                21
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR"

(iii) HYPOTHETICAL: NO (iv) ANTI-SENSE: YES (xi) SEQUENCE DESCRIPTION: SEQ ID NO:4:

```
ATCCAAAATC TCATCAATTT C                                                21
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR."

(iii) HYPOTHETICAL: NO (iv) ANTI-SENSE: YES (xi) SEQUENCE DESCRIPTION: SEQ ID NO:5:

```
ATGAGTCCTT ACATGTGA                                                    18
```

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear

```
        (ii) MOLECULE TYPE: other nucleic acid
             (A) DESCRIPTION: /desc = "Oligonucleotide primer for
                 PCR."

(iii) HYPOTHETICAL: NO (iv) ANTI-SENSE: YES (xi) SEQUENCE DESCRIPTION: SEQ ID NO:6:

GGGAGCTCGA ATTCCATGGC CTCAGCAGCA GCAGTTGCAA ACTAT                    45

(2) INFORMATION FOR SEQ ID NO:7:

(i) SEQUENCE CHARACTERISTICS:
             (A) LENGTH: 4254 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Nicotiana tabacum (ix) FEATURE:
             (A) NAME/KEY: CDS
             (B) LOCATION: join(1217..1327, 1455..1718, 1806..2182,
                 2259
                     ..2477, 2609..2747, 2903..3148, 3262..3558)

(xi) SEQUENCE DESCRIPTION: SEQ ID NO:7:

AAGCTTTATG AATTAGATGT AAAAAGACGC AAACTACTTA TATATATTAC CAAAGTAACT     60

TGAAAGTTTA AAATTTCAAT TAGAACTATA GTAGGGTAAA ACTGTCTATT TAAAATCAGT    120

ATTTAAAAAG GCATGAGCGA AAGATGAGGC GTTTTATCTA ACACGAAGCG AGGTGTAAGC    180

CCCATGGTGT TTTATTTTTA TATTTTATAA ATTTATAAAA TCATTATATA AATCAGAAAA    240

ATACACTAAA ATTGTGAAAA GTTAAAGAAA ATTATAGAAT TAATATATAT ATATATATAT    300

ATATATATAT ATATATATAT ATATATATAT ATATATATAT AAATGTATGT GTGTGTGTGT    360

GTGTACATGC GCGCGCGACC ATGCAACTTT TTTTTCTTGA AAAAATAAAA GGCGTAAAGA    420

TACATTATAC CTATGTCATC AAAACAATAT AAAAACTAGA GCGATACCAA AAGAAATTTT    480

AAATTCAAAA ACTAACTTGA AATTAATATA TTTAAAATTT CATTTTTTTT TGTGTGGAGA    540

AAACAAAGCA TAACACTTTG CTTTGTAACA CTTTGCCTAG GTGAATGTCA GGGCTTATGC    600

TCCACGATAC TTATGCCCTG CCAGTACACC TCGCGGTGGG ACTCGCTCAA AAAACGTCTT    660

TGTTGTGAGA AATTGCAATT TTGAACCTCT ACAATTTCGA CAAAACCTTG GTTCGTGAAA    720

ACTGTTTGAT TAACTTTTAG ACCATCCAGT CAATTTAACT CTAAACTGAC CTAAATAAAT    780

ACTACGTACA CTAGTCTTTA AGTTCATCAA AGTGGACTCT GCATTAATAA TTGAAATTTA    840

TGCCGCAACA ATGACATTAG GTTTTATAAA TAAAGTAATA GGAATTTGAT AGTTCCAGGA    900

AACAACTCTA CAGTACTCCC TTATTTTGTG CCTTTTTAAA TAATATTATT CAGTTGACGA    960

AACAAATAAA TAAATATTT GGGAAACTGG ATCAATAGAC CCCAGACGCC AACAATGAAT   1020

CAAAAGGCTG CTAGCTAGTG TAAAGTCTAG TAAGGCAACT GGGAAATTAA ATGATTAGGT   1080

GCTTTTGATC AATTACATTA ACTAGTCTCT CACCACTATA TATACTTGTC CCTTCTCTTC   1140

CATTTAAGTA GAGTTCCTTT CTTTCTTCCT TAAAACTTAA AAGAACAAGT AAAAATACAC   1200
```

```
TCATCTTTAA TTAGCA ATG GCC TCA GCA GCA GTT GCA AAC TAT GAA GAA       1249
               Met Ala Ser Ala Ala Val Ala Asn Tyr Glu Glu
                 1               5                  10

GAG ATT GTT CGC CCC GTC GCC GAC TTC TCC CCT AGT CTC TGG GGT GAT    1297
Glu Ile Val Arg Pro Val Ala Asp Phe Ser Pro Ser Leu Trp Gly Asp
             15                  20                  25

CAG TTC CTT TCA TTC TCC ATT GAT AAT CAG GTAATTAAC TAATACTAGT       1347
Gln Phe Leu Ser Phe Ser Ile Asp Asn Gln
             30                  35

ATTCTTTATT TATATTTATA GTTTGTTCTC CATTGATAAT CAGGTAGTTT ATTTATGTTG   1407

AACAACATTA ATTTTGCTAA TTTCAGTTTA ATGTACATTA CATATAG GTT GCG GAA    1463
                                                    Val Ala Glu
                                                            40

AAG TAT ATA TAT GCT CAA GAG ATT GAA GCA TTG AAG GAA CAA ACG AGG    1511
Lys Tyr Ile Tyr Ala Gln Glu Ile Glu Ala Leu Lys Glu Gln Thr Arg
             45                  50                  55

AGT ATG CTG TTA GCA ACC GGA AGG AAA TTG GCC GAT ACA TTG AAT TTG    1559
Ser Met Leu Leu Ala Thr Gly Arg Lys Leu Ala Asp Thr Leu Asn Leu
             60                  65                  70

ATT GAC ATT ATT GAA CGC CTT GGT ATA TCC TAC CAC TTT GAG AAA GAA    1607
Ile Asp Ile Ile Glu Arg Leu Gly Ile Ser Tyr His Phe Glu Lys Glu
         75                  80                  85

ATT GAT GAG ATT TTG GAT CAG ATT TAC AAC CAA AAC TCA AAC TGC AAT    1655
Ile Asp Glu Ile Leu Asp Gln Ile Tyr Asn Gln Asn Ser Asn Cys Asn
         90                  95                 100

GAT TTG TGC ACC TCT GCA CTT CAA TTT CGA TTG CTC AGG CAA CAC GGT    1703
Asp Leu Cys Thr Ser Ala Leu Gln Phe Arg Leu Leu Arg Gln His Gly
105                 110                 115                 120

TTC AAC ATC TCT CCT GGTAAGTTCA TCATGAAGTT GTTAAAATTA TTATCCATTT    1758
Phe Asn Ile Ser Pro
                125

ATTGGAAGAA GGCTAATTCA TCTTGAGTTT TCTTTCTTGA AATACCA GAA ATT TTC    1814
                                                    Glu Ile Phe

AGC AAA TTC CAA GAT GAA AAT GGC AAA TTC AAG GAG TCT CTT GCT AGT    1862
Ser Lys Phe Gln Asp Glu Asn Gly Lys Phe Lys Glu Ser Leu Ala Ser
            130                 135                 140

GAT GTC TTA GGA TTA TTA AAC TTG TAT GAA GCT TCA CAT GTA AGG ACT    1910
Asp Val Leu Gly Leu Leu Asn Leu Tyr Glu Ala Ser His Val Arg Thr
145                 150                 155                 160

CAT GCT GAC GAT ATC TTA GAA GAC GCA CTT GCT TTC TCC ACT ATC CAT    1958
His Ala Asp Asp Ile Leu Glu Asp Ala Leu Ala Phe Ser Thr Ile His
                165                 170                 175

CTT GAA TCT GCA GCT CCA CAT TTG AAA TCT CCA CTT AGG GAG CAA GTG    2006
Leu Glu Ser Ala Ala Pro His Leu Lys Ser Pro Leu Arg Glu Gln Val
            180                 185                 190

ACA CAT GCC CTT GAG CAA TGT TTG CAC AAG GGT GTT CCT AGA GTC GAG    2054
Thr His Ala Leu Glu Gln Cys Leu His Lys Gly Val Pro Arg Val Glu
            195                 200                 205

ACC CGA TTC TTC ATC TCA TCA ATC TAT GAC AAG GAA CAA TCG AAG AAT    2102
Thr Arg Phe Phe Ile Ser Ser Ile Tyr Asp Lys Glu Gln Ser Lys Asn
            210                 215                 220

AAT GTG TTA CTT CGA TTT GCC AAA TTG GAT TTC AAC TTG CTC CAG ATG    2150
Asn Val Leu Leu Arg Phe Ala Lys Leu Asp Phe Asn Leu Leu Gln Met
225                 230                 235                 240

TTG CAC AAA CAA GAA CTT GCT CAA GTA TCA AG GTGCGATATA              2192
Leu His Lys Gln Glu Leu Ala Gln Val Ser Arg
            245                 250

TAAAAACGAT GAACCCTTTT TGATTCATCA TATCTCAAGT ACTCATGTTA ATTTCTTATG  2252
```

```
CTGCAG G TGG TGG AAA GAT TTG GAT TTT GTA ACA ACA CTT CCA TAT GCT      2301
        Trp Trp Lys Asp Leu Asp Phe Val Thr Thr Leu Pro Tyr Ala
                    255                 260                 265

AGA GAT CGA GTA GTT GAA TGC TAC TTT TGG GCA TTA GGA GTT TAT TTT      2349
Arg Asp Arg Val Val Glu Cys Tyr Phe Trp Ala Leu Gly Val Tyr Phe
                270                 275                 280

GAG CCT CAA TAC TCT CAA GCT CGC GTC ATG CTC GTT AAG ACC ATA TCA      2397
Glu Pro Gln Tyr Ser Gln Ala Arg Val Met Leu Val Lys Thr Ile Ser
                285                 290                 295

ATG ATT TCG ATT GTC GAT GAC ACC TTT GAT GCT TAC GGT ACA GTT AAA      2445
Met Ile Ser Ile Val Asp Asp Thr Phe Asp Ala Tyr Gly Thr Val Lys
                300                 305                 310

GAA CTT GAG GCA TAC ACA GAT GCC ATA CAA AG  GTATGAACTT               2487
Glu Leu Glu Ala Tyr Thr Asp Ala Ile Gln Arg
            315                 320

CATCAATTCA CTTATTCCTT GATAGTGAAT GTCGTCGTGA AAAGATTAAG ACGAATTTCT    2547

ACTCATTATA GTTGTGCTCT TTCAAAATGC ATGAATTCAC CTTAATTTTG TCATCCTGCA    2607

G A TGG GAT ATC AAC GAA ATT GAT CGG CTT CCT GAT TAC ATG AAA ATC      2654
    Trp Asp Ile Asn Glu Ile Asp Arg Leu Pro Asp Tyr Met Lys Ile
                325                 330                 335

AGT TAT AAA GCT ATT CTA GAT CTC TAC AAG GAT TAT GAA AAG GAA TTG      2702
Ser Tyr Lys Ala Ile Leu Asp Leu Tyr Lys Asp Tyr Glu Lys Glu Leu
340                 345                 350                 355

TCT AGT GCC GGA AGA TCT CAT ATT GTC TGC CAT GCA ATA GAA AGA          2747
Ser Ser Ala Gly Arg Ser His Ile Val Cys His Ala Ile Glu Arg
                360                 365                 370

GTATGTTCGA GCAACTTAAC TATCGAAATA CATTTTTTCC TTAATCCATT TCTCACTTTG    2807

GTTTACCTTG TGTTCGTCTT TTAGTGATTA GAAACTTGAT ACAGTTCAAT CAATATTTTC    2867

TAACACTTGA ACACATATAT GTTTTGTATT CACAG ATG AAA GAA GTA GTA AGA      2920
                                      Met Lys Glu Val Val Arg
                                                          375

AAT TAT AAT GTC GAG TCA ACA TGG TTT ATT GAA GGA TAT ATG CCA CCT      2968
Asn Tyr Asn Val Glu Ser Thr Trp Phe Ile Glu Gly Tyr Met Pro Pro
                380                 385                 390

GTT TCT GAA TAC CTA AGC AAT GCA CTA GCA ACT ACC ACA TAT TAC TAC      3016
Val Ser Glu Tyr Leu Ser Asn Ala Leu Ala Thr Thr Thr Tyr Tyr Tyr
                395                 400                 405

CTC GCG ACA ACA TCG TAT TTG GGC ATG AAG TCT GCC ACG GAG CAA GAT      3064
Leu Ala Thr Thr Ser Tyr Leu Gly Met Lys Ser Ala Thr Glu Gln Asp
            410                 415                 420

TTT GAG TGG TTG TCA AAG AAT CCA AAA ATT CTT GAA GCT AGT GTA ATT      3112
Phe Glu Trp Leu Ser Lys Asn Pro Lys Ile Leu Glu Ala Ser Val Ile
425                 430                 435                 440

ATA TGT CGA GTT ATC GAT GAC ACA GCC ACG TAC GAG  GTATGATTTG          3158
Ile Cys Arg Val Ile Asp Asp Thr Ala Thr Tyr Glu
                445                 450

CATCTCAAGA AATTATATCA TTATATGGGA TTTGGACAAA CAAAGTGTTG CGACGACAAT    3218

TAAGGCAATA TAAAAGCTAA CCTTTAATTT ATCTGCTTTC TAG GTT GAG AAA AGC      3273
                                                 Val Glu Lys Ser
                                                             455

AGG GGA CAA ATT GCA ACT GGA ATT GAG TGC TGC ATG AGA GAT TAT GGT      3321
Arg Gly Gln Ile Ala Thr Gly Ile Glu Cys Cys Met Arg Asp Tyr Gly
                460                 465                 470

ATA TCA ACA AAA GAG GCA ATG GCT AAA TTT CAA AAT ATG GCT GAG ACA      3369
Ile Ser Thr Lys Glu Ala Met Ala Lys Phe Gln Asn Met Ala Glu Thr
                475                 480                 485

GCA TGG AAA GAT ATT AAT GAA GGA CTT CTT AGG CCC ACT CCC GTC TCT      3417
```

```
Ala Trp Lys Asp Ile Asn Glu Gly Leu Leu Arg Pro Thr Pro Val Ser
    490                 495                 500

ACA GAA TTT TTA ACT CCT ATT CTC AAT CTT GCT CGT ATT GTT GAG GTT       3465
Thr Glu Phe Leu Thr Pro Ile Leu Asn Leu Ala Arg Ile Val Glu Val
505                 510                 515                 520

ACA TAT ATA CAC AAT CTA GAT GGA TAC ACT CAT CCG GAG AAA GTC TTA       3513
Thr Tyr Ile His Asn Leu Asp Gly Tyr Thr His Pro Glu Lys Val Leu
                525                 530                 535

AAA CCT CAC ATT ATT AAC CTA CTT GTG GAC TCC ATC AAA ATT TGA           3558
Lys Pro His Ile Ile Asn Leu Leu Val Asp Ser Ile Lys Ile *
                540                 545                 550

GCTGCCATTT GTTGCTCATC TCAAGGAAAC TTCATTCTTC TTTGTGCAGT TGTGCAGTAG     3618

ACTTCCTAAC TAGGAGCTTC TTAAGATCCT TGTAAGAAAT AATCTTCAAG TGTTATGAAT     3678

CCGCATTGTG GAGAAATCTT TTTATATGAC AATAAGTTAT GTTATGAAGA ATGTTATGGG     3738

GGTCTCTTAT GACCTATTTG TCAGTGTATG AAGTAATCTG AGCCTGTCGA AAAAAAAGGT     3798

AATCTGAGCC TTTTGCTCGT CCTTCCTTTA GTATTTCTTT TTATCATACT TGGTCTCACA     3858

AAAATTAGTT TTTGGCACCT TTGTTTTTCC TTGTGGCGCA TGTGTATATA CATCTGAAAC     3918

ATATACTTAA AGGTTAAGAG GACATTGACA TATTGAATCA ACACTAGTGT TATTGGCATA     3978

CAGGAGAGAA TCTATGTGTA AAGGACGGGG TGGAACCCCA CCCACAAGAC TTGGTCGAGA     4038

CTATTGTTTA TCGAAAAAAC GGTACAGTTG AATTTATACG TGGTTTATAG ACAAGTGAAT     4098

TAATTTGATC CTAAAATAAT AGGCGAATTA GATAAAAATG TAATTCTTAG CCTTGAGTTG     4158

GAGACGAAAT AGCAGAAATA GTGATTCCAG GAGAAAGGCT TTCGGGTACC ACAACAATGA     4218

TATCAAAAAA TAAAAAGATA AAATTGTATT AAGCTT                               4254

(2) INFORMATION FOR SEQ ID NO:8:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO:8:

Met Ala Ser Ala Ala Val Ala Asn Tyr Glu Glu Glu Ile Val Arg Pro
1               5                   10                  15

Val Ala Asp Phe Ser Pro Ser Leu Trp Gly Asp Gln Phe Leu Ser Phe
                20                  25                  30

Ser Ile Asp Asn Gln Val Ala Glu Lys Tyr Ile Tyr Ala Gln Glu Ile
            35                  40                  45

Glu Ala Leu Lys Glu Gln Thr Arg Ser Met Leu Leu Ala Thr Gly Arg
    50                  55                  60

Lys Leu Ala Asp Thr Leu Asn Leu Ile Asp Ile Ile Glu Arg Leu Gly
65                  70                  75                  80

Ile Ser Tyr His Phe Glu Lys Glu Ile Asp Glu Ile Leu Asp Gln Ile
                85                  90                  95

Tyr Asn Gln Asn Ser Asn Cys Asn Asp Leu Cys Thr Ser Ala Leu Gln
            100                 105                 110

Phe Arg Leu Leu Arg Gln His Gly Phe Asn Ile Ser Pro Glu Ile Phe
        115                 120                 125

Ser Lys Phe Gln Asp Glu Asn Gly Lys Phe Lys Glu Ser Leu Ala Ser
    130                 135                 140

Asp Val Leu Gly Leu Leu Asn Leu Tyr Glu Ala Ser His Val Arg Thr
```

```
                145                 150                 155                 160
His Ala Asp Asp Ile Leu Glu Asp Ala Leu Ala Phe Ser Thr Ile His
                    165                 170                 175
Leu Glu Ser Ala Ala Pro His Leu Lys Ser Pro Leu Arg Glu Gln Val
                180                 185                 190
Thr His Ala Leu Glu Gln Cys Leu His Lys Gly Val Pro Arg Val Glu
            195                 200                 205
Thr Arg Phe Phe Ile Ser Ser Ile Tyr Asp Lys Glu Gln Ser Lys Asn
        210                 215                 220
Asn Val Leu Leu Arg Phe Ala Lys Leu Asp Phe Asn Leu Leu Gln Met
225                 230                 235                 240
Leu His Lys Gln Glu Leu Ala Gln Val Ser Arg Trp Trp Lys Asp Leu
                245                 250                 255
Asp Phe Val Thr Thr Leu Pro Tyr Ala Arg Asp Arg Val Val Glu Cys
                260                 265                 270
Tyr Phe Trp Ala Leu Gly Val Tyr Phe Glu Pro Gln Tyr Ser Gln Ala
            275                 280                 285
Arg Val Met Leu Val Lys Thr Ile Ser Met Ile Ser Ile Val Asp Asp
            290                 295                 300
Thr Phe Asp Ala Tyr Gly Thr Val Lys Glu Leu Glu Ala Tyr Thr Asp
305                 310                 315                 320
Ala Ile Gln Arg Trp Asp Ile Asn Glu Ile Asp Arg Leu Pro Asp Tyr
                325                 330                 335
Met Lys Ile Ser Tyr Lys Ala Ile Leu Asp Leu Tyr Lys Asp Tyr Glu
                340                 345                 350
Lys Glu Leu Ser Ser Ala Gly Arg Ser His Ile Val Cys His Ala Ile
            355                 360                 365
Glu Arg Met Lys Glu Val Val Arg Asn Tyr Asn Val Glu Ser Thr Trp
        370                 375                 380
Phe Ile Glu Gly Tyr Met Pro Pro Val Ser Glu Tyr Leu Ser Asn Ala
385                 390                 395                 400
Leu Ala Thr Thr Thr Tyr Tyr Tyr Leu Ala Thr Thr Ser Tyr Leu Gly
                405                 410                 415
Met Lys Ser Ala Thr Glu Gln Asp Phe Glu Trp Leu Ser Lys Asn Pro
            420                 425                 430
Lys Ile Leu Glu Ala Ser Val Ile Ile Cys Arg Val Ile Asp Asp Thr
        435                 440                 445
Ala Thr Tyr Glu Val Glu Lys Ser Arg Gly Gln Ile Ala Thr Gly Ile
    450                 455                 460
Glu Cys Cys Met Arg Asp Tyr Gly Ile Ser Thr Lys Glu Ala Met Ala
465                 470                 475                 480
Lys Phe Gln Asn Met Ala Glu Thr Ala Trp Lys Asp Ile Asn Glu Gly
                485                 490                 495
Leu Leu Arg Pro Thr Pro Val Ser Thr Glu Phe Leu Thr Pro Ile Leu
            500                 505                 510
Asn Leu Ala Arg Ile Val Glu Val Thr Tyr Ile His Asn Leu Asp Gly
        515                 520                 525
Tyr Thr His Pro Glu Lys Val Leu Lys Pro His Ile Ile Asn Leu Leu
    530                 535                 540
Val Asp Ser Ile Lys Ile
545                 550
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR."

(iii) HYPOTHETICAL: NO (iv) ANTI-SENSE: NO (xi) SEQUENCE DESCRIPTION: SEQ ID NO:9:

CGTTGGATCC CCACCTCATC CGAAATGAAC                       30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR."

(iii) HYPOTHETICAL: NO (iv) ANTI-SENSE: YES (xi) SEQUENCE DESCRIPTION: SEQ ID NO:10:

GGCTGAGCTC CTGGACGCAG AGATCAAACC                       30

(2) INFORMATION FOR SEQ ID NO:11:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR (reverse)."

(iii) HYPOTHETICAL: NO (iv) ANTI-SENSE: YES (xi) SEQUENCE DESCRIPTION: SEQ ID NO:11:

GCCGGATCCT TATGACTAGT TGCACCACCA CGCAGCAAAC TG            42

(2) INFORMATION FOR SEQ ID NO:12:

(i) SEQUENCE CHARACTERISTICS:
        (A) LENGTH: 593 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Phytophthora parasitica (ix) FEATURE:
    (A) NAME/KEY: CDS
    (B) LOCATION: 207..563

(xi) SEQUENCE DESCRIPTION: SEQ ID NO:12:

```
GTCGACGAAA GCCGAAGTGC GTGGCAGATC TTGCCGTTCG AATGCTACGC GCCACGGCAA         60

AACCTACACG GTACAACAGC TTCAAATAAA CCTGCAAGCG AGCCGCCAGC CCAACTCCAG        120

CTAGTCAAGC CTAGTTTGCC TCCAACTGCC ATTGTGCAAT TTGCTCTCAT CCACACCCAC        180

CCCACTTCTC CCCCACCTCA TCCGAA ATG AAC TTC CGC GCT CTG TTC GCC GCC        233
                             Met Asn Phe Arg Ala Leu Phe Ala Ala
                                 555                 560
```

```
ACC GTC GCC GCC CTC GTC GGC TCC ACC TCC GCC ACC ACG TGC ACC ACC         281
Thr Val Ala Ala Leu Val Gly Ser Thr Ser Ala Thr Thr Cys Thr Thr
            565                 570                 575

ACG CAG CAA ACT GCG GCG TAC GTG GCG CTC GTA AGC ATC CTC TCG GAC         329
Thr Gln Gln Thr Ala Ala Tyr Val Ala Leu Val Ser Ile Leu Ser Asp
            580                 585                 590

ACG TCG TTC AAC CAG TGC TCG ACG GAC TCT GGC TAC TCA ATG CTG ACG         377
Thr Ser Phe Asn Gln Cys Ser Thr Asp Ser Gly Tyr Ser Met Leu Thr
            595                 600                 605

GCC ACC TCG TTG CCC ACG ACG GAG CAG TAC AAG CTC ATG TGC GCG TCG         425
Ala Thr Ser Leu Pro Thr Thr Glu Gln Tyr Lys Leu Met Cys Ala Ser
            610                 615                 620

ACG GCG TGC AAG ACG ATG ATC AAC AAG ATC GTG ACG CTG AAC CCG CCC         473
Thr Ala Cys Lys Thr Met Ile Asn Lys Ile Val Thr Leu Asn Pro Pro
625                 630                 635                 640

GAC TGC GAG TTG ACG GTG CCT ACG AGC GGC CTG GTA CTC AAC GTG TTC         521
Asp Cys Glu Leu Thr Val Pro Thr Ser Gly Leu Val Leu Asn Val Phe
            645                 650                 655

ACG TAC GCG AAC GGG TTC TCG TCT ACG TGC GCG TCA CTG TAA              563
Thr Tyr Ala Asn Gly Phe Ser Ser Thr Cys Ala Ser Leu  *
            660                 665                 670

GCGGGTTTGA TCTCTGCGTC CAGAATCGAT                                         593
```

(2) INFORMATION FOR SEQ ID NO:13:

(i) SEQUENCE CHARACTERISTICS:
       (A) LENGTH: 118 amino acids
       (B) TYPE: amino acid
       (D) TOPOLOGY: linear (ii) MOLECULE TYPE: protein (xi) SEQUENCE DESCRIPTION: SEQ ID NO:13:

```
Met Asn Phe Arg Ala Leu Phe Ala Ala Thr Val Ala Ala Leu Val Gly
  1               5                  10                  15

Ser Thr Ser Ala Thr Thr Cys Thr Thr Thr Gln Gln Thr Ala Ala Tyr
             20                  25                  30

Val Ala Leu Val Ser Ile Leu Ser Asp Thr Ser Phe Asn Gln Cys Ser
         35                  40                  45

Thr Asp Ser Gly Tyr Ser Met Leu Thr Ala Thr Ser Leu Pro Thr Thr
     50                  55                  60

Glu Gln Tyr Lys Leu Met Cys Ala Ser Thr Ala Cys Lys Thr Met Ile
 65                  70                  75                  80

Asn Lys Ile Val Thr Leu Asn Pro Pro Asp Cys Glu Leu Thr Val Pro
                 85                  90                  95
```

```
Thr Ser Gly Leu Val Leu Asn Val Phe Thr Tyr Ala Asn Gly Phe Ser
            100                 105                 110

Ser Thr Cys Ala Ser Leu
            115
```